(12) United States Patent
Woodruff et al.

(10) Patent No.: US 6,309,524 B1
(45) Date of Patent: *Oct. 30, 2001

(54) METHODS AND APPARATUS FOR PROCESSING THE SURFACE OF A MICROELECTRONIC WORKPIECE

(75) Inventors: Daniel J. Woodruff; Kyle M. Hanson; Thomas H. Oberlitner; LinLin Chen; John M. Pedersen, all of Kalispell, MT (US); Vladimir Zila, Scarborough (CA)

(73) Assignee: Semitool, Inc., Kalispell, MT (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/386,610

(22) Filed: Aug. 31, 1999

Related U.S. Application Data

(63) Continuation of application No. PCT/US99/15847, filed on Jul. 12, 1999, which is a continuation of application No. 09/113,723, filed on Jul. 10, 1998, now Pat. No. 6,080,291.
(60) Provisional application No. 60/111,232, filed on Dec. 7, 1998, and provisional application No. 60/119,668, filed on Feb. 11, 1999.

(51) Int. Cl.$^7$ ............................ C25D 17/04; C25D 17/06

(52) U.S. Cl. ................................ 204/297.1; 204/297.09

(58) Field of Search ............................ 8204/297 R, 279, 204/297.01, 297.09, 297.06, 297.1

(56) References Cited

U.S. PATENT DOCUMENTS

| | | | |
|---|---|---|---|
| 4,137,867 | 2/1979 | Aigo | 118/627 |
| 4,246,088 | 1/1981 | Murphy et al. | 204/181 R |
| 4,259,166 | 3/1981 | Whitehurst | 204/279 |
| 4,304,641 | 12/1981 | Grandia et al. | 204/23 |
| 4,341,629 | 7/1982 | Uhlinger | 210/128 |
| 4,466,864 | 8/1984 | Bacon et al. | 204/115 |
| 4,576,685 | 3/1986 | Goffredo et al. | 204/30 |
| 4,685,414 | 8/1987 | DiRico | 118/46 |
| 4,913,085 | 4/1990 | Vohringer et al. | 118/312 |
| 5,135,636 | * 8/1992 | Yee et al. | 205/96 |

(List continued on next page.)

FOREIGN PATENT DOCUMENTS

| | | |
|---|---|---|
| WO99/25904 | 5/1999 | (WO). |
| WO99/25905 | 8/1999 | (WO). |
| WO00/32835 | 6/2000 | (WO). |

*Primary Examiner*—Donald R. Valentine
*Assistant Examiner*—Erica Smith-Hicks
(74) *Attorney, Agent, or Firm*—Perkins Coie LLP

(57) ABSTRACT

A reactor for plating a metal onto a surface of a workpiece is set forth. The reactor comprises a reactor bowl including an electroplating solution disposed therein and an anode disposed in the reactor bowl in contact with the electroplating solution. A contact assembly is spaced from the anode within the reactor bowl. The contact assembly includes a plurality of contacts disposed to contact a peripheral edge of the surface of the workpiece to provide electroplating power to the surface of the workpiece. The contacts execute a wiping action against the surface of the workpiece as the workpiece is brought into engagement therewith. The contact assembly also including a barrier disposed interior of the plurality of contacts. The barrier includes a member disposed to engage the surface of the workpiece to assist in isolating the plurality of contacts from the electroplating solution. In one embodiment, the plurality of contacts are in the form of discrete flexures while in another embodiment the plurality of contacts are in the form of a Belleville ring contact. A flow path may be provided in the contact assembly for providing a purging gas to the plurality of contacts and the peripheral edge of the workpiece. The purging gas may be used to assist in the formation of the barrier of the contact assembly. A combined electroplating/electroless plating tool and method are also set forth.

39 Claims, 26 Drawing Sheets

U.S. PATENT DOCUMENTS

| | | | |
|---|---|---|---|
| 5,227,041 | * 7/1993 | Brogden et al. | 204/297 R |
| 5,271,953 | 12/1993 | Litteral | 427/8 |
| 5,344,491 | 9/1994 | Katou | 118/695 |
| 5,441,629 | 8/1995 | Kosaki | 205/148 |
| 5,443,707 | 8/1995 | Mori | 204/242 |
| 5,447,615 | 9/1995 | Ishida | 204/224 R |
| 5,522,975 | * 6/1996 | Andricacos et al. | 204/297 R |
| 5,597,460 | 1/1997 | Reynolds | 514/352 |
| 5,597,836 | 1/1997 | Hackler et al. | 514/352 |
| 5,609,239 | 3/1997 | Schlecker | 198/680 |
| 5,670,034 | 9/1997 | Lowery | 205/143 |
| 5,744,019 | * 4/1998 | Ang | 205/96 |
| 5,747,098 | 5/1998 | Larson | 427/158 |
| 5,776,327 | 7/1998 | Botts et al. | 205/96 |
| 5,788,829 | 8/1998 | Joshi et al. | 205/96 |
| 5,843,296 | 12/1998 | Greenspan | 205/68 |
| 5,904,827 | 5/1999 | Reynolds | 205/68 |
| 5,932,077 | 8/1999 | Reynolds | 204/224 R |
| 6,080,291 | 6/2000 | Woodruff et al. | 204/297.1 |
| 6,139,712 | 10/2000 | Patton et al. | |

* cited by examiner

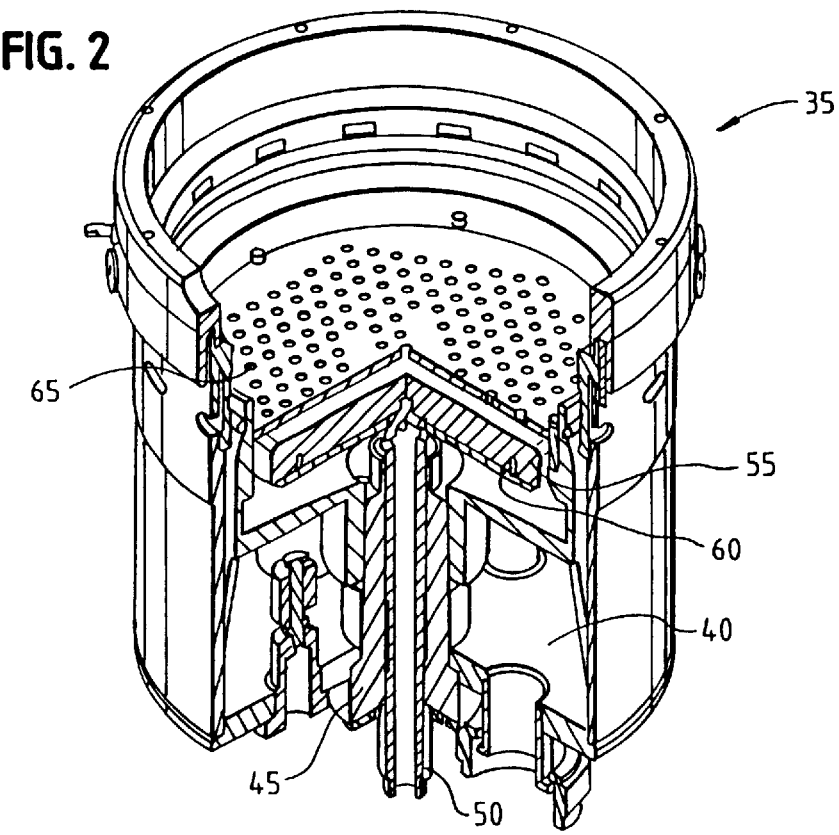
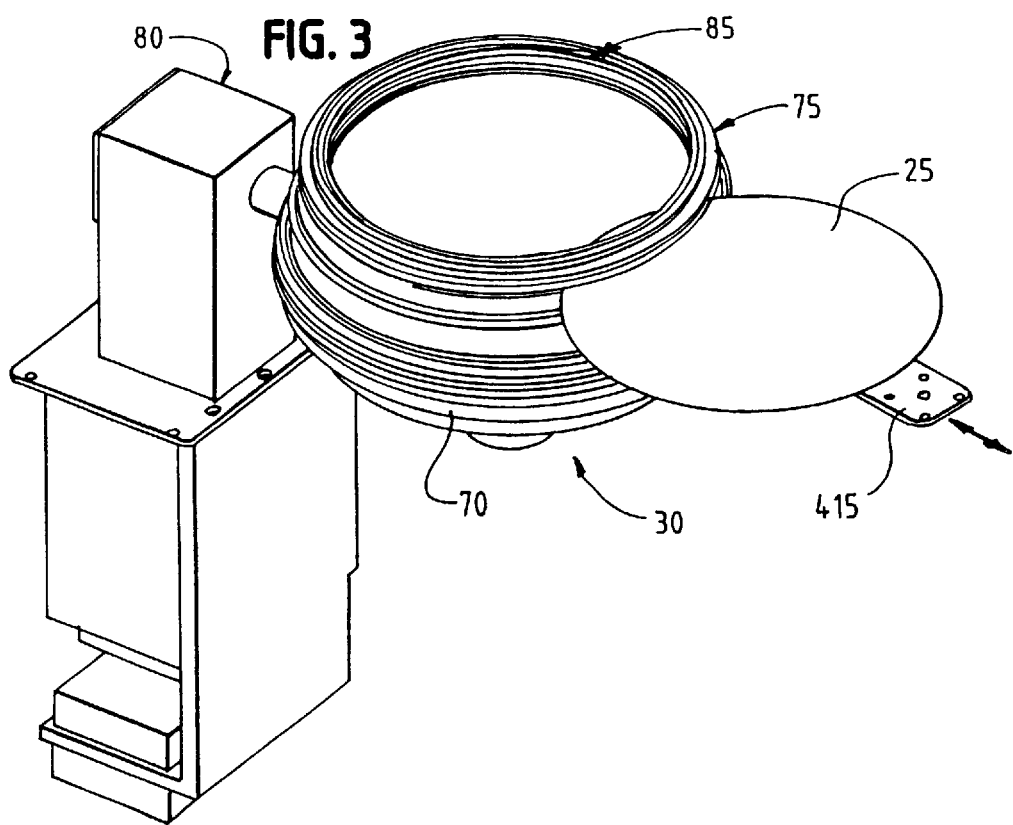

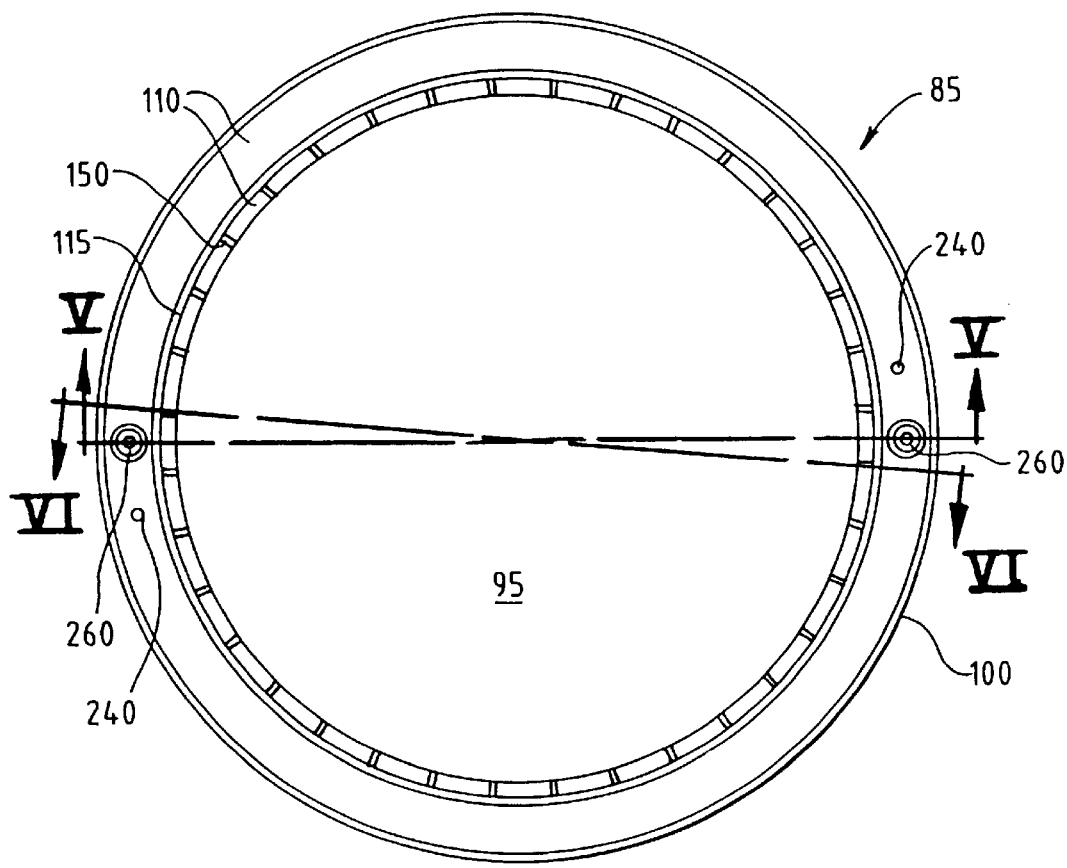
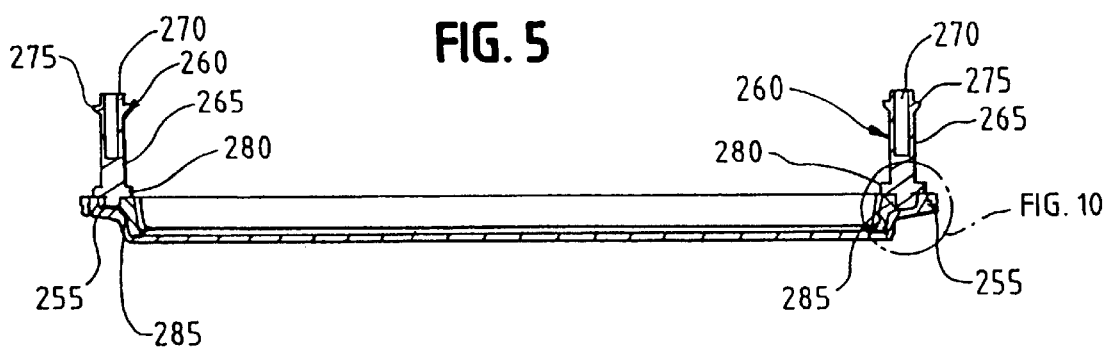

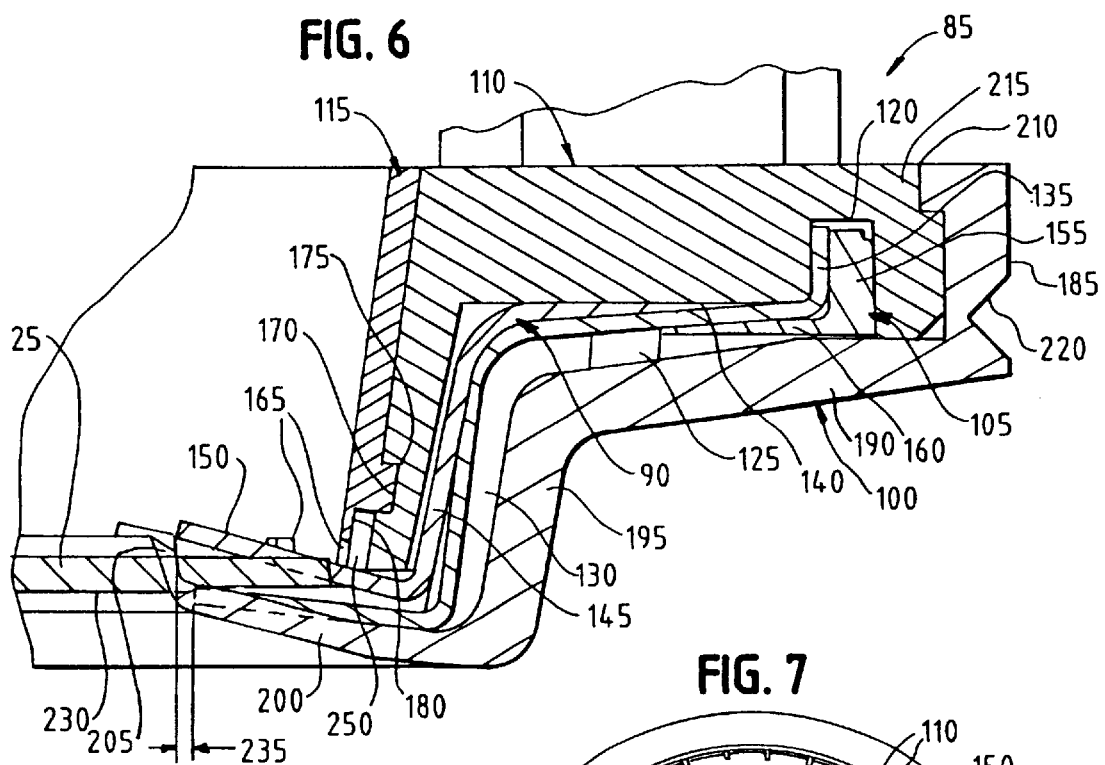
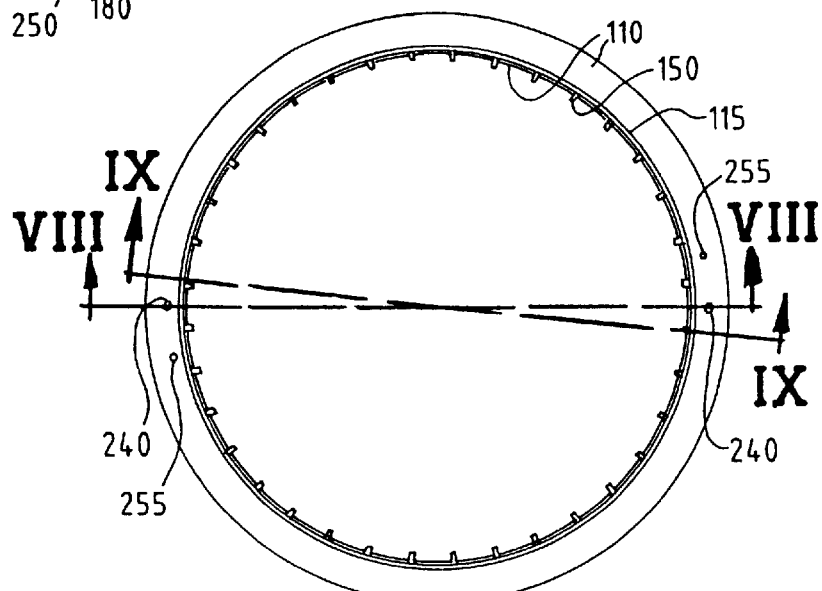
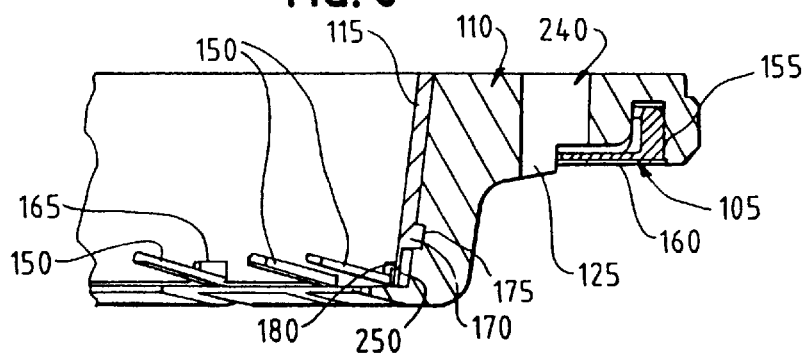

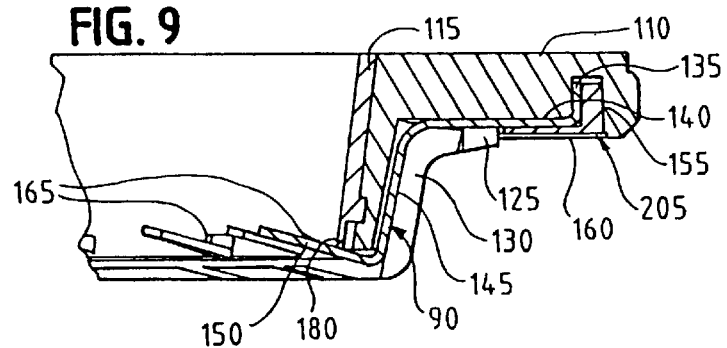
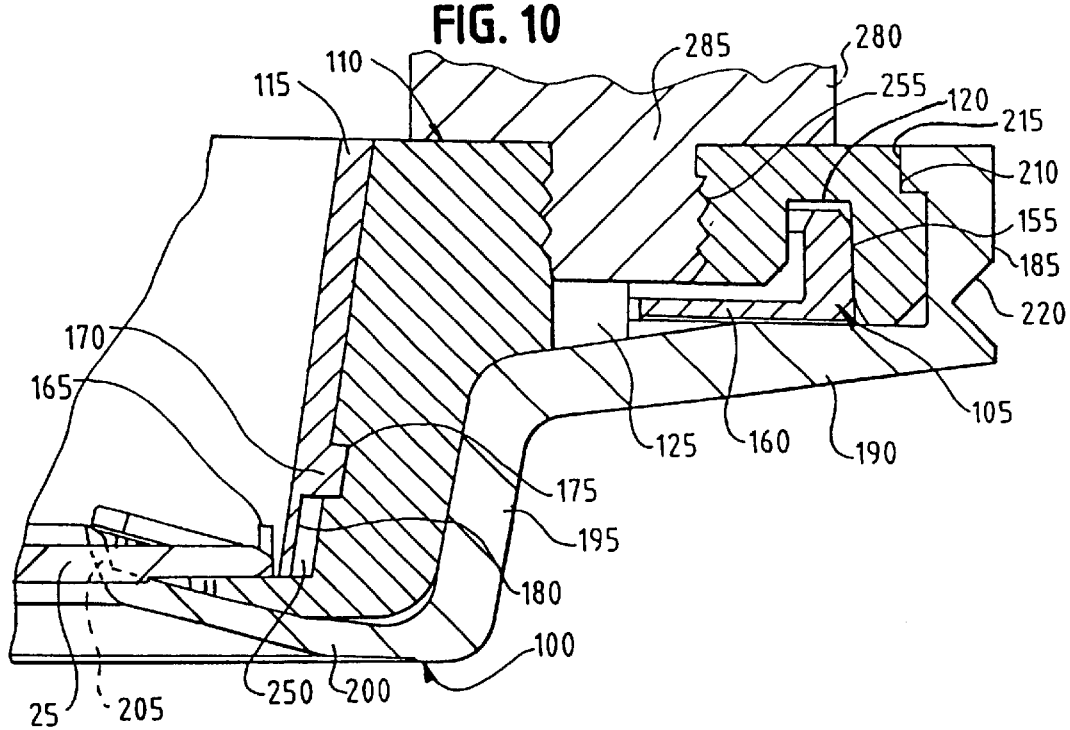
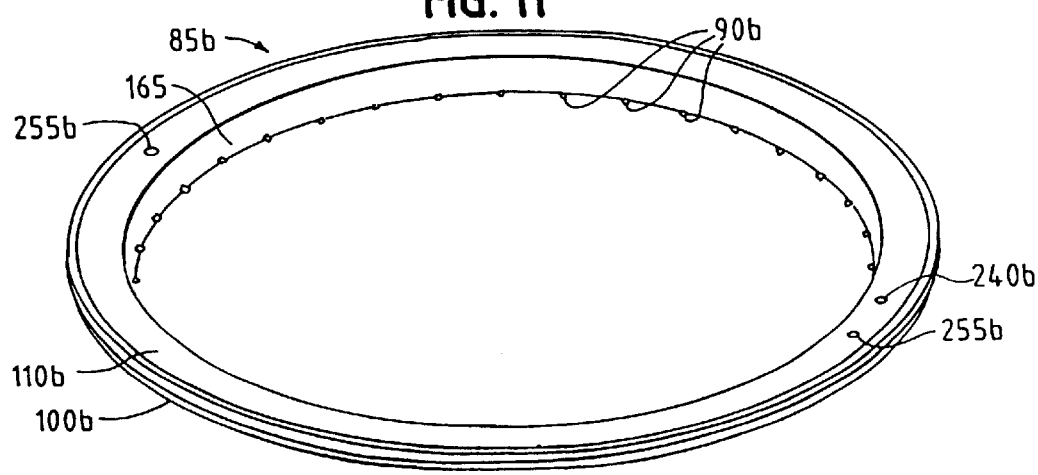

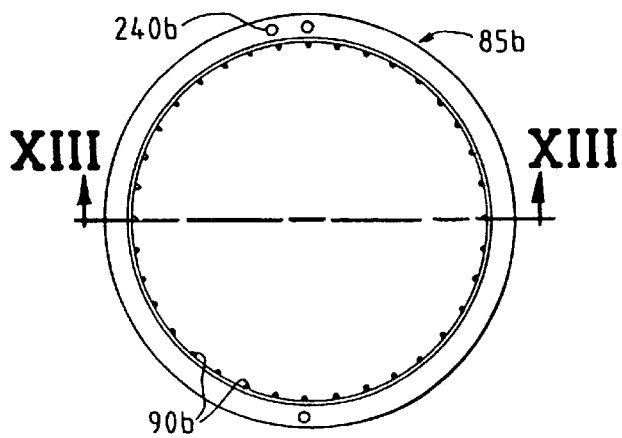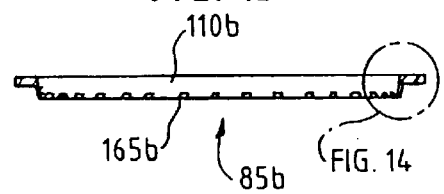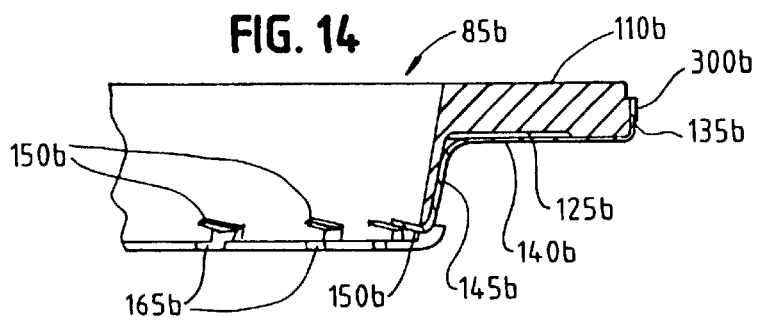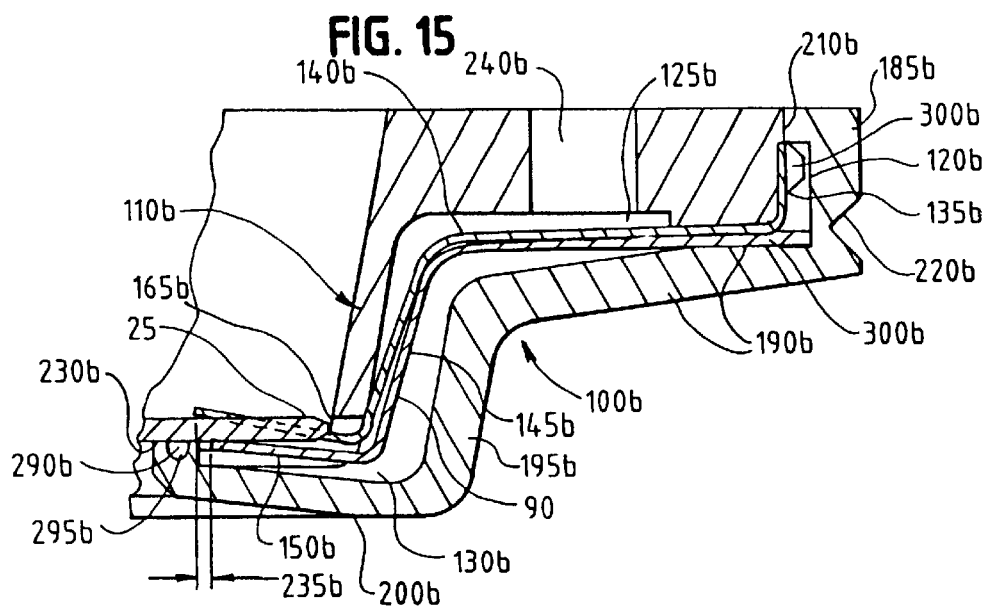

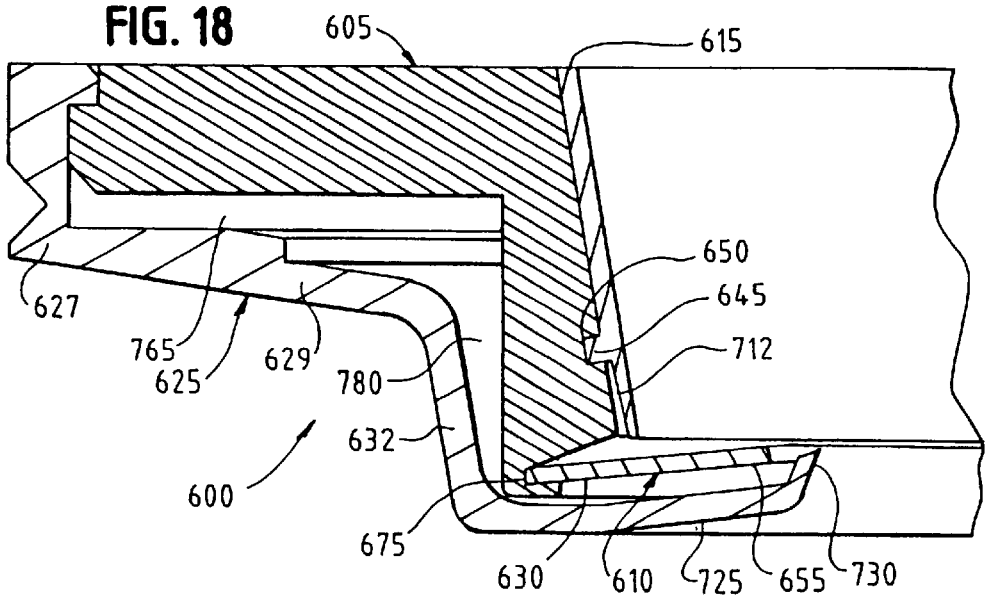
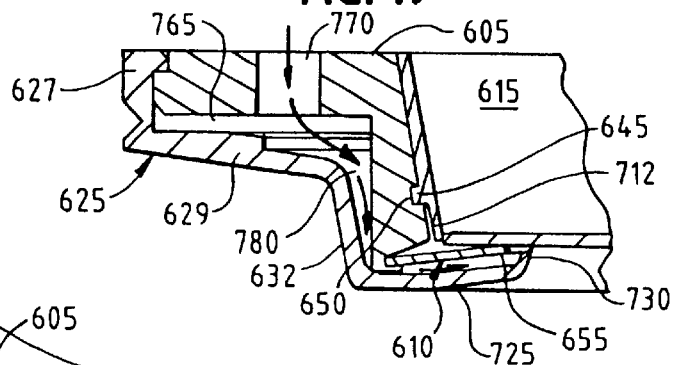
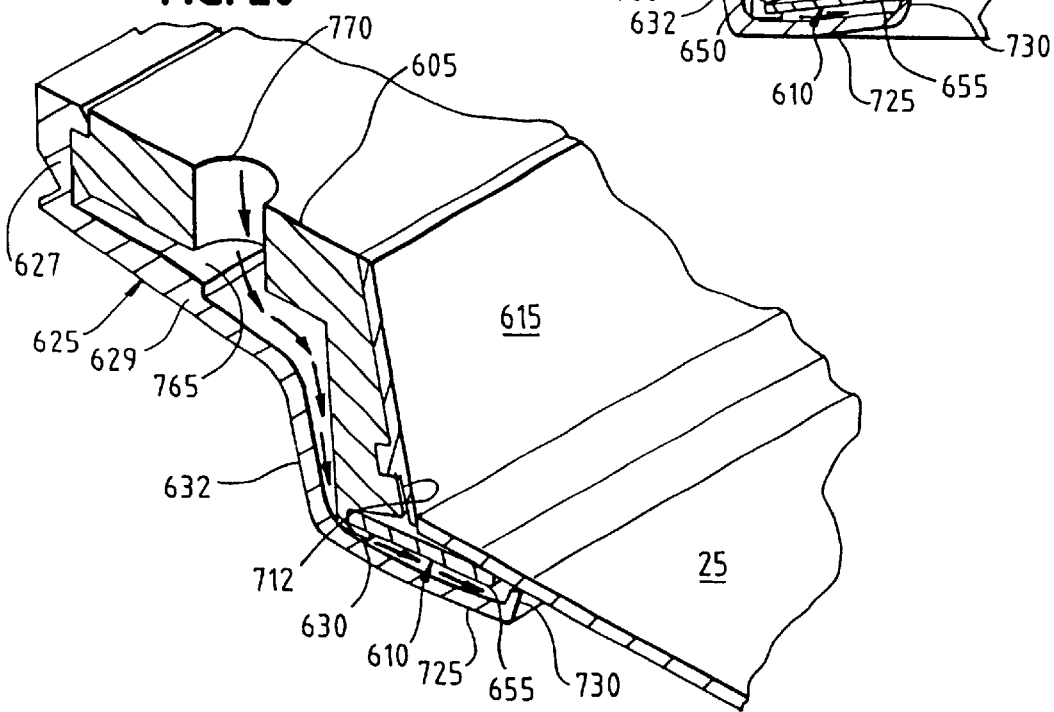

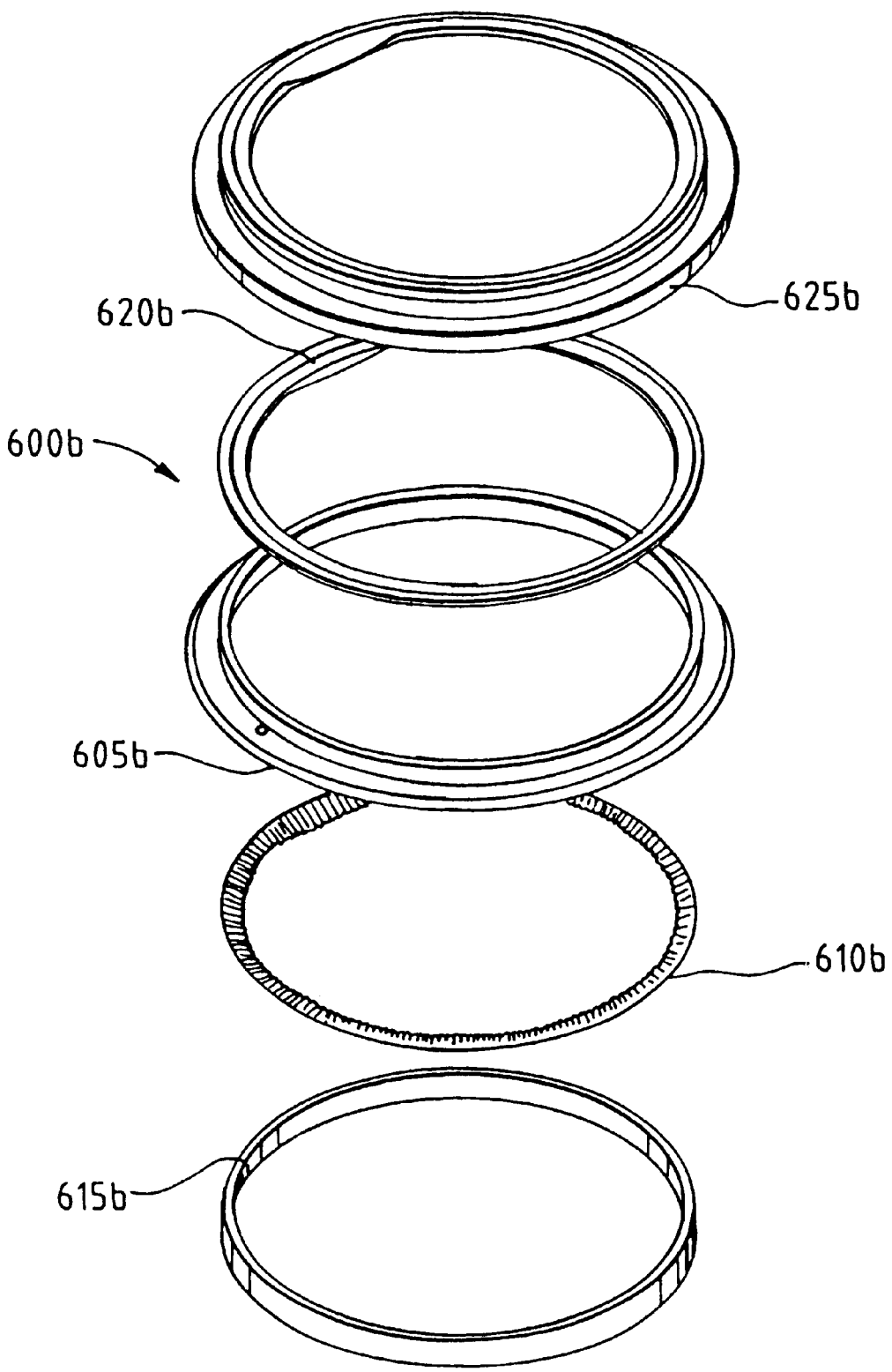

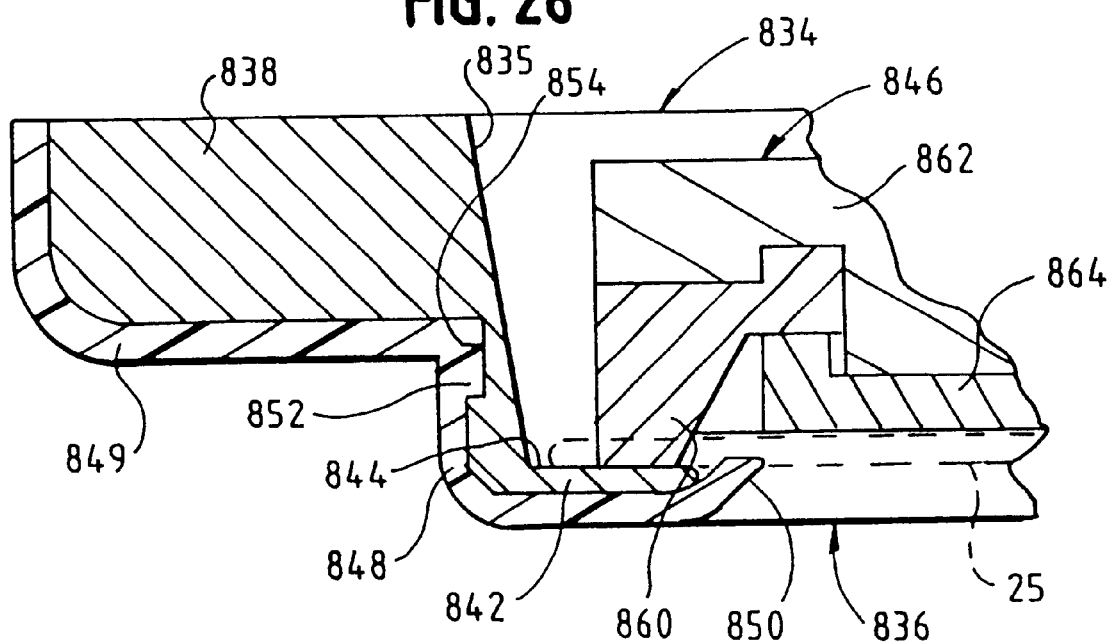
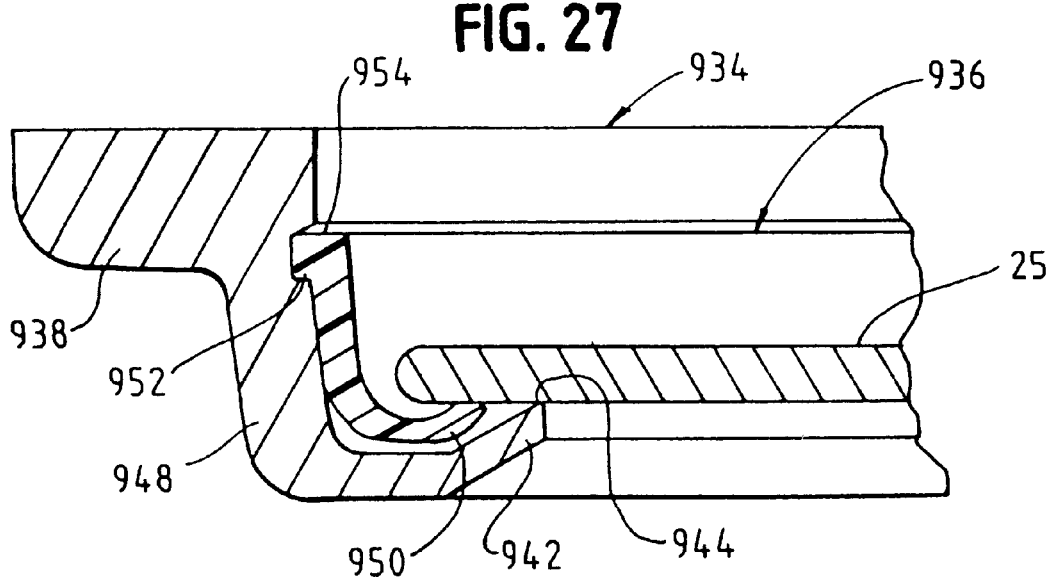

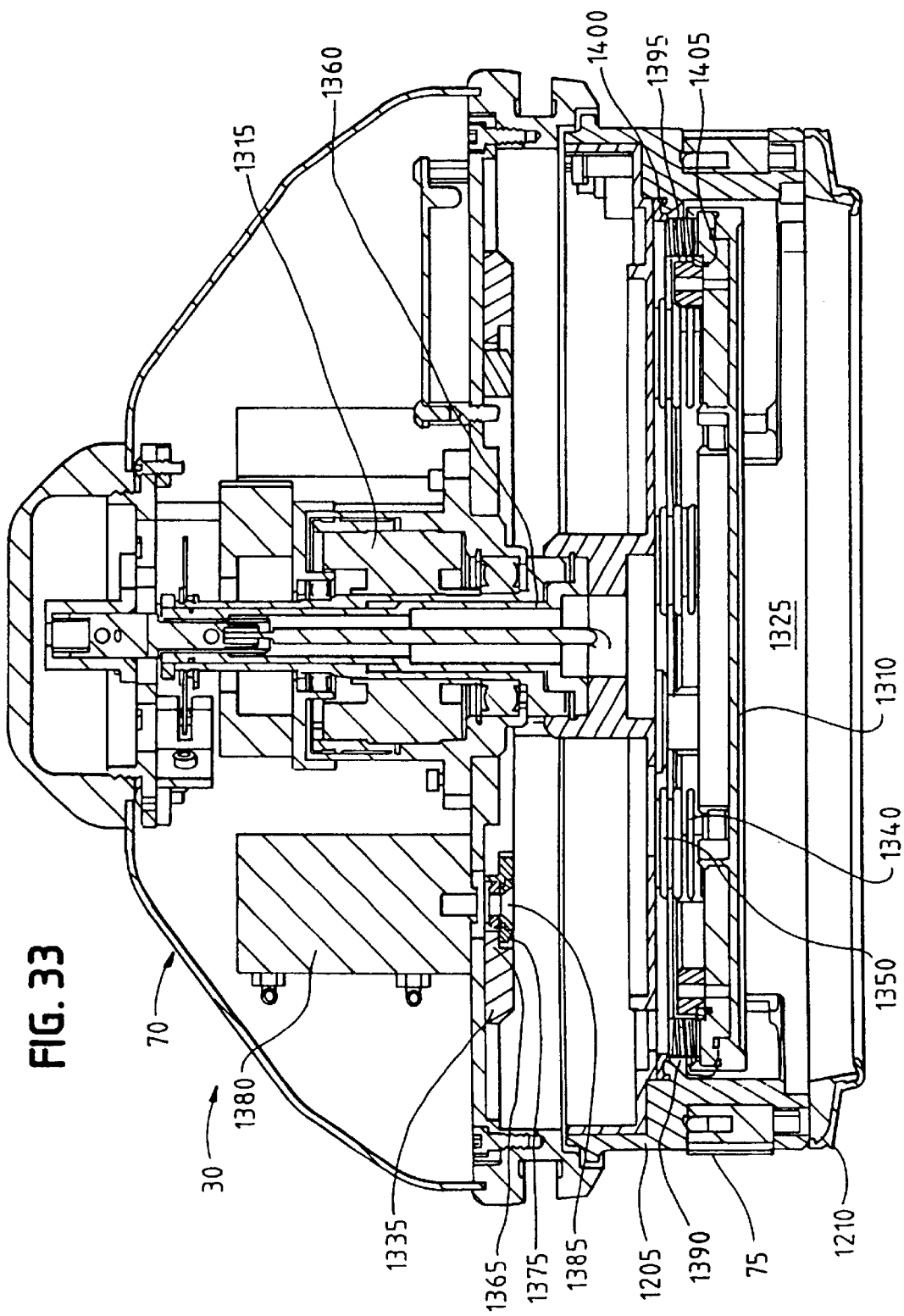

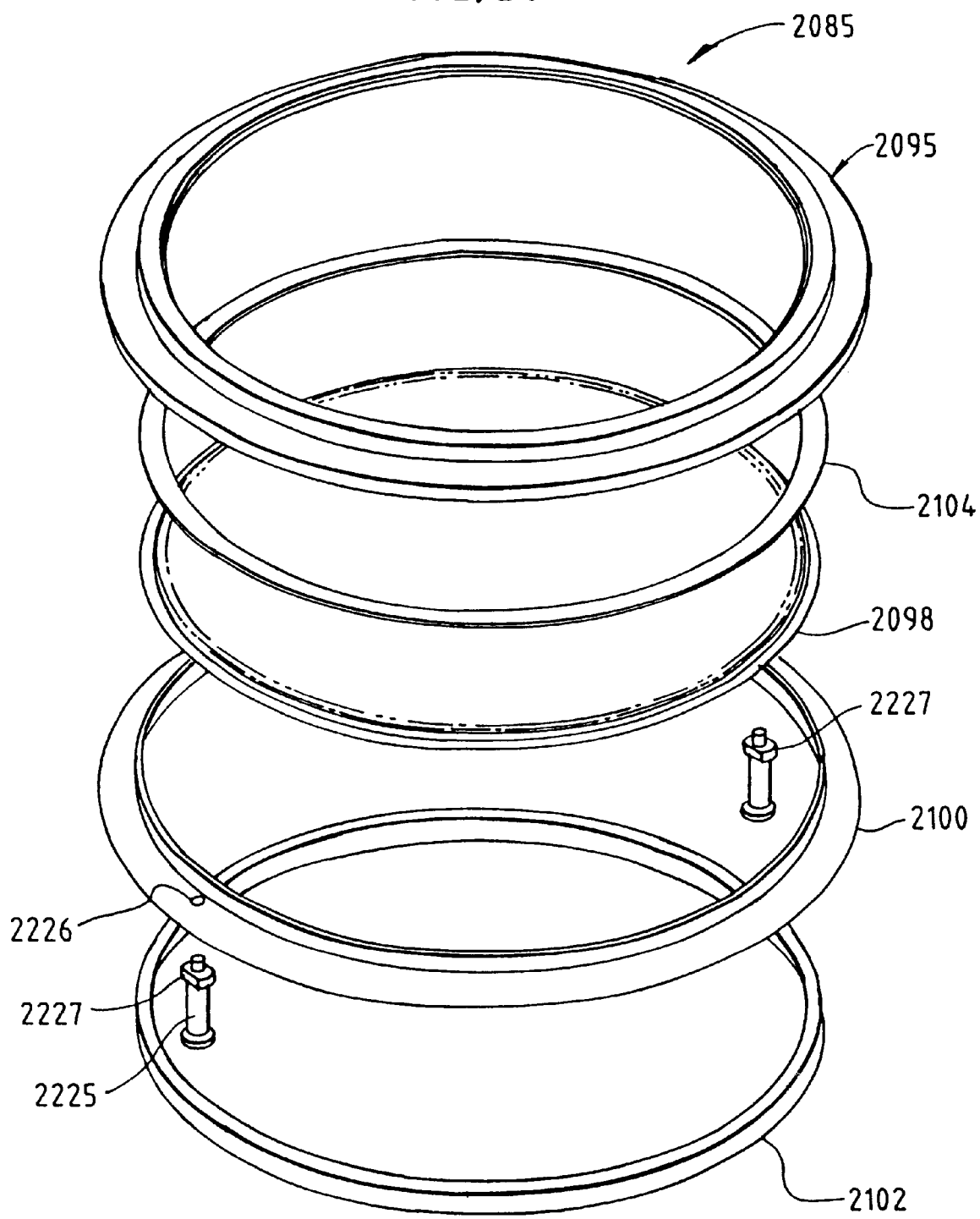

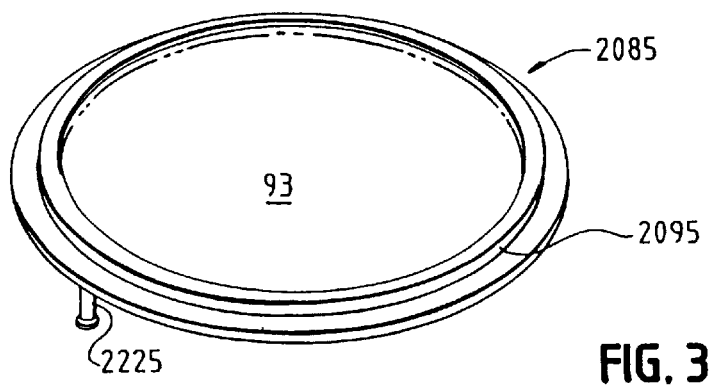
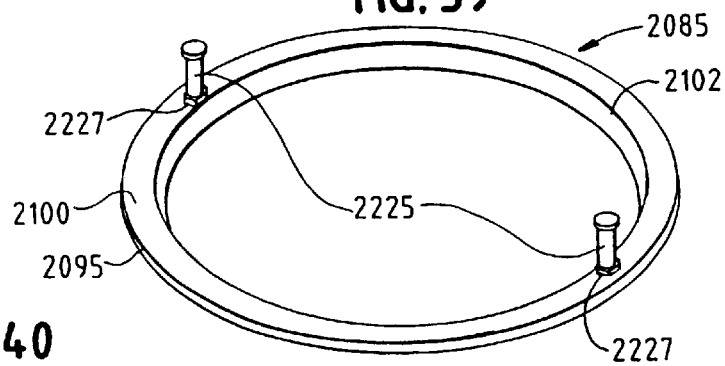
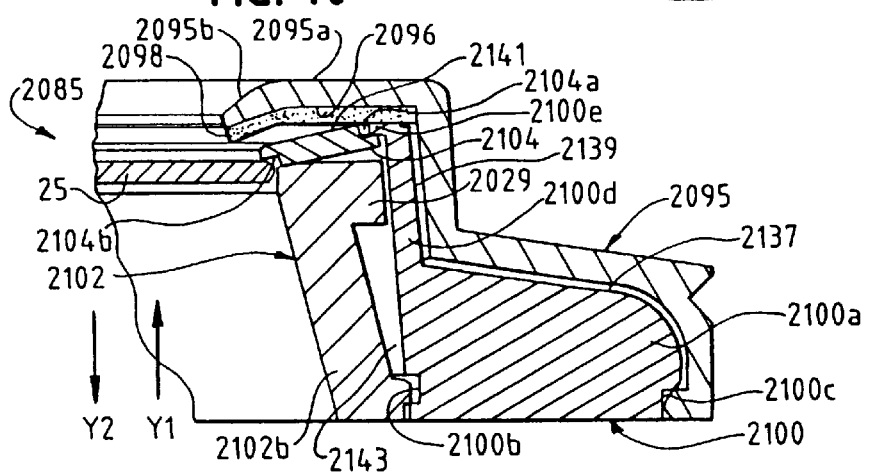
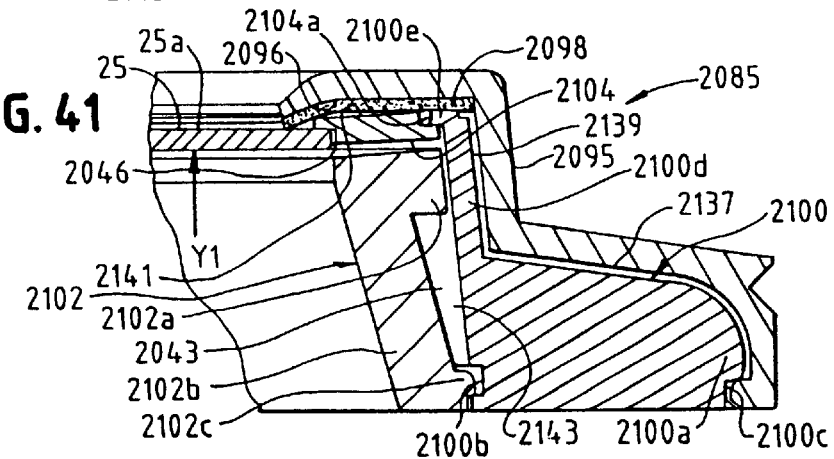

METHODS AND APPARATUS FOR PROCESSING THE SURFACE OF A MICROELECTRONIC WORKPIECE

CROSS-REFERENCE TO RELATED APPLICATIONS

This is a continuation application of International PCT Patent Application No. PCT/US99/15847, designating the U.S., filed Jul. 12, 1999, entitled METHOD AND APPARATUS FOR COPPER PLATING USING ELECTROLESS PLATING AND ELECTROPLATING, which is a continuation of U.S. patent application Ser. No. 09/113,723, filed Jul. 10, 1998, now U.S. Pat. No. 6,080,291 U.S. patent application Ser. No. 60/111,232, filed Dec. 7, 1998 and U.S. patent application Ser. No. 60/119,668, filed Feb. 11, 1999.

BACKGROUND OF THE INVENTION

Production of semiconductor integrated circuits and other microelectronic devices from workpieces such as semiconductor wafers typically requires formation of one or more metal layers on the wafer. These metal layers are used, for example, to electrically interconnect the various devices of the integrated circuit. Further, the structures formed from the metal layers may constitute microelectronic devices such as read/write heads, etc.

The microelectronic manufacturing industry has applied a wide range of metals to form such structures. These metals include, for example, nickel, tungsten, solder, platinum, and copper. Further, a wide range of processing techniques have been used to deposit such metals. These techniques include, for example, chemical vapor deposition (CVD), physical vapor deposition (PVD), electroplating, and electroless plating. Of these techniques, electroplating and electroless plating tend to be the most economical and, as such, the most desirable. Electroplating and electroless plating can be used in the deposition of blanket metal layers as well as patterned metal layers.

One of the most popular process sequences used by the microelectronic manufacturing industry to deposit a metal onto semiconductor wafers is referred to as "damascene" processing. In such processing holes, commonly called "vias", trenches and/or other recesses are formed onto a workpiece and filled with a metal, such as copper. In the damascene process, the wafer is first provided with a metallic seed layer which is used to conduct electrical current during a subsequent metal electroplating step. If a metal such as copper is used, the seed layer is disposed over a barrier layer material, such as Ti, TiN, etc. The seed layer is a very thin layer of metal which can be applied using one or more of several processes. For example, the seed layer of metal can be laid down using physical vapor deposition or chemical vapor deposition processes to produce a layer on the order of 1,000 angstroms thick. The seed layer can advantageously be formed of copper, gold, nickel, palladium, or other metals. The seed layer is formed over a surface which is convoluted by the presence of the vias, trenches, or other recessed device features.

A metal layer is then electroplated onto the seed layer in the form of a blanket layer. The blanket layer is plated to form an overlying layer, with the goal of providing a metal layer that fills the trenches and vias and extends a certain amount above these features. Such a blanket layer will typically have a thickness on the order of 10,000 to 15,000 angstroms (1–1.5 microns).

After the blanket layer has been electroplated onto the semiconductor wafer, excess metal material present outside of the vias, trenches, or other recesses is removed. The metal is removed to provide a resulting pattern of metal layer in the semiconductor integrated circuit being formed. The excess plated material can be removed, for example, using chemical mechanical planarization. Chemical mechanical planarization is a processing step which uses the combined action of a chemical removal agent and an abrasive which grinds and polishes the exposed metal surface to remove undesired parts of the metal layer applied in the electroplating step.

The electroplating of the semiconductor wafers takes place in a reactor assembly. In such an assembly an anode electrode is disposed in a plating bath, and the wafer with the seed layer thereon is used as a cathode. Only a lower face of the wafer contacts the surface of the plating bath. The wafer is held by a support system that also conducts the requisite electroplating power (e.g., cathode current) to the wafer. The support system may comprise conductive fingers that secure the wafer in place and also contact the wafer seed layer in order to conduct electrical current for the plating operation. One embodiment of a reactor assembly is disclosed in U.S. Ser. No. 08/988,333 filed Sep. 30, 1997 entitled "Semiconductor Plating System Workpiece Support Having Workpiece—Engaging Electrodes With Distal Contact Part and Dielectric Cover."

Several technical problems must be overcome in designing reactors used in the electroplating of semiconductor wafers. Utilization of a small number of discrete electrical contacts (e.g., 6 contacts) with the seed layer about the perimeter of the wafer ordinarily produces higher current densities near the contact points than at other portions of the wafer. This non-uniform distribution of current across the wafer, in turn, causes non-uniform deposition of the plated metallic material. Current thieving, effected by the provision of electrically-conductive elements other than those which contact the seed layer, can be employed near the wafer contacts to minimize such non-uniformity. But such thieving techniques add to the complexity of electroplating equipment, and increase maintenance requirements.

Another problem with electroplating of wafers concerns efforts to prevent the electric contacts themselves from being plated during the electroplating process. Any material plated to the electrical contacts must be removed to prevent changing contact performance. While it is possible to provide sealing mechanisms for discrete electrical contacts, such arrangements typically cover a significant area of the wafer surface, and can add complexity to the electrical contact design.

In addressing a further problem, it is sometimes desirable to prevent electroplating on the exposed barrier layer near the edge of the semiconductor wafer. Electroplated material may not adhere well to the exposed barrier layer material, and is therefore prone to peeling off in subsequent wafer processing steps. Further, metal that is electroplated onto the barrier layer within the reactor may flake off during the electroplating process thereby adding particulate contaminants to the electroplating bath. Such contaminants can adversely affect the overall electroplating process.

The specific metal to be electroplated can also complicate the electroplating process. For example, electroplating of certain metals typically requires use of a seed layer having a relatively high electrical resistance. As a consequence, use of the typical plurality of electrical wafer contacts (for example, six (6) discrete contacts) may not provide adequate uniformity of the plated metal layer on the wafer.

Beyond the contact related problems discussed above, there are also other problems associated with electroplating reactors. As device sizes decrease, the need for tighter control over the processing environment increases. This includes control over the contaminants that affect the electroplating process. The moving components of the reactor, which tend to generate such contaminants, should therefore be subject to strict isolation requirements.

Still further, existing electroplating reactors are often difficult to maintain and/or reconfigure for different electroplating processes. Such difficulties must be overcome if an electroplating reactor design is to be accepted for large-scale manufacturing.

One aspect of the present invention is directed to an improved electroplating apparatus having one or more of the following features: an improved workpiece contact assembly, a processing head having a quick-disconnect contact assembly construction, and/or a processing head having effective isolation of the moving components from the processing environment.

One drawback associated with copper deposition by electroplating is the fact that for very small features on microelectronic workpieces (sub 0.1 micron features), copper deposition by electroplating can lack conformality with the side walls of high aspect ratio vias and trenches, and can produce voids in the formed interconnects and plugs (vias). This is often due to the non-conformality of the copper seed layer deposited by PVD or CVD as a result, the seed layer may not be thick enough to carry the current to the bottom of high aspect ratio features.

An alternate process for depositing copper onto a microelectronic workpiece is known as "electroless" plating. A method of electroless plating of copper metallization onto microelectronic workpieces is disclosed in the article "Sub-Half Micron Electroless Cu Metallization," by V. M. Dubin, et al., as published in the Materials Research Society Symposium Proceedings, volume 427, Advances Metallization For Future ULSI, 1996, herein incorporated by reference. The article describes the potential advantages of electroless Cu metallization as including lower tool costs, lower processing temperatures, higher quality deposits, superior uniformity of plating, and better via/trench filling capability.

According to the disclosed procedure, a blanket electroless Cu deposition was performed for via and trench filling on a workpiece having a Cu seed layer. The Cu seed layer was previously deposited by sputtering or contact displacement (wet activation process). An aluminum sacrificial layer was sputtered onto the Cu seed layer. Collimated Ti/N, uncollimated Ti, and uncollimated. Ta were used as diffusion barrier/adhesion promoter layers. After the electroless deposition of the Cu layer, chemical/mechanical polishing of the copper layer was performed to obtain inlaid copper metallization. A selective electroless CoW passivation layer was deposited on the inlaid Cu metallization.

According to the method disclosed in the foregoing article, the etching of the Al sacrificial layer in the same electroless Cu plating bath without transferring the wafer results in the catalytic Cu surface not being exposed to air. This purportedly avoids oxidation before the electroless Cu deposition is undertaken. After etching of the Al sacrificial seed layer, the catalytic seed layer acts as a catalytic material for electroless Cu deposition. Also, according to the disclosed method, annealing of the seedibarrier layer system at 300° C. in a vacuum improved adhesion of the seed layer.

Additionally, a small amount of surfactant and stabilizer was added to the copper plating solution in order to control surface tension and to retard hydrogen inclusion in the deposits, as well as to increase solution stability. Examples of surfactants are: RE 610, polyethylenglycol,NCW-601A, Triton X-100. Examples of stabilizers disclosed are: Neocuproine, 2,2'dipyridyl, CN—, Rhodanine.

Other patents which describe and teach electroless metallization techniques include U.S. Pat. No. 5,500,315; U.S. Pat. No. 5,310,580; U.S. Pat. No. 5,389,496; and U.S. Pat. No. 5,139,818, all of which are hereby incorporated by reference.

Whereas electroless plating of copper on microelectronic workpieces offers advantages such as good conformality the electroless deposition rate of copper is generally lower than that produced by electroplating. Accordingly, another aspect of the present invention recognizes the desirability of achieving the advantageous conformality of the deposited copper in small and/or high aspect ratio features, such as vias and trenches, while at the same time having an increased overall deposition rate for increased microelectronic production throughput. This aspect of the present invention also recognizes the desirability of providing an electroless plating reactor which can be incorporated into an automated microelectronic processing tool.

SUMMARY OF THE INVENTIONS

A reactor for plating a metal onto a surface of a workpiece is set forth. The reactor comprises a reactor bowl including an electroplating solution disposed therein and an anode disposed in the reactor bowl in contact with the electroplating solution. A contact assembly is spaced from the anode within the reactor bowl. The contact assembly includes a plurality of contacts disposed to contact a peripheral edge of the surface of the workpiece to provide electroplating power to the surface of the workpiece. The contacts execute a wiping action against the surface of the workpiece as the workpiece is brought into engagement therewith. The contact assembly also including a barrier disposed interior of the plurality of contacts. The barrier includes a member disposed to engage the surface of the workpiece to assist in isolating the plurality of contacts from the electroplating solution. In one embodiment, the plurality of contacts are in the form of discrete flexures while in another embodiment, the plurality of contacts are in the form of a Belleville ring contact. A flow path may be provided in the contact assembly for providing a purging gas to the plurality of contacts and the peripheral edge of the workpiece. The purging gas may be used to assist in the formation of the barrier of the contact assembly.

In accordance with a further aspect of the present invention, the contact assembly is connected within the reactor assembly by one rmore latching mechanisms. The latching mechanisms allow easy replacement of the contact assembly with another contact assembly of the same or of a different type. Given the construction of the disclosed contact assemblies, replacement with the same type of contact assembly reduces or otherwise eliminates the need for recalibration of the plating system thereby reducing down time of the reactor.

In accordance with further aspect of the inventive reactor, the reactor may comprise a processing head including the contact assembly. More particularly, the processing head may include a stator portion and a rotor portion, the rotor portion comprising the contact assembly. The contact assembly may be detachably connected to the rotor portion by at least one latching mechanism.

The reactor as may also include a backing member and a drive mechanism in an assembly in which the backing member and contact assembly are moved relative to one another by the drive mechanism between a workpiece loading state and a workpiece processing state. In the workpiece processing state, the workpiece is urged against the plurality of contacts of the contact assembly by the backing member. To reduce the risk of contamination from particles released by the drive mechanism, the drive mechanism may be substantially surrounded by a bellows member.

An integrated tool for plating a workpiece is also set forth. The integrated tool comprises a first processing chamber for plating the workpiece using an electroless plating process and a second processing chamber for plating the workpiece using an electroplating process. A robotic transfer mechanism is used that is programmed to transfer a workpiece to the first processing chamber for electroless plating thereof and, in a subsequent operation, to transfer the workpiece to the second processing chamber for electroplating thereof. A plating process that may be implemented on the foregoing tool is set forth, although the disclosed process is independent of the processing tool.

BRIEF DESCRIPTION OF THE DRAWINGS

FIG. 2 illustrates a specific construction of one embodiment of a reactor bowl suitable for use in the assembly illustrated in FIG. 1.

FIG. 3 illustrates one embodiment of a reactor head, comprised of a stationary assembly and a rotor assembly that is suitable for use in the assembly illustrated in FIG. 1.

FIGS. 4–10 illustrate one embodiment of a contact assembly using flexure contacts that is suitable for use in the reactor assembly illustrated in FIG. 1.

FIGS. 11–15 illustrate another embodiment of a contact assembly using flexure contacts that is suitable for use in the reactor assembly illustrated in FIG. 1.

FIGS. 18–20 illustrate one embodiment of a contact assembly using a "Belleville ring" contact structure, such as one of those illustrated in FIGS. 15–17, that is suitable for use in the reactor assembly illustrated in FIG. 1.

FIGS. 21–23 illustrate another embodiment of a contact assembly using a "Belleville ring" contact structure, such as one of those illustrated in FIGS. 15–17, that is suitable for use in the reactor assembly illustrated in FIG. 1.

FIGS. 26 and 27 illustrate another embodiment of a contact assembly that is suitable for use in the reactor assembly illustrated in FIG. 1.

FIG. 33 is a cross-sectional view of the reactor head illustrating the disposition of the reactor head in a condition in which it may accept a workpiece.

FIGS. 37–42 illustrate various embodiments of workpiece holders suitable for use in the electroless plating reactor of FIG. 36.

DETAILED DESCRIPTION OF THE INVENTIONS

Basic Reactor Components

Figure 1:
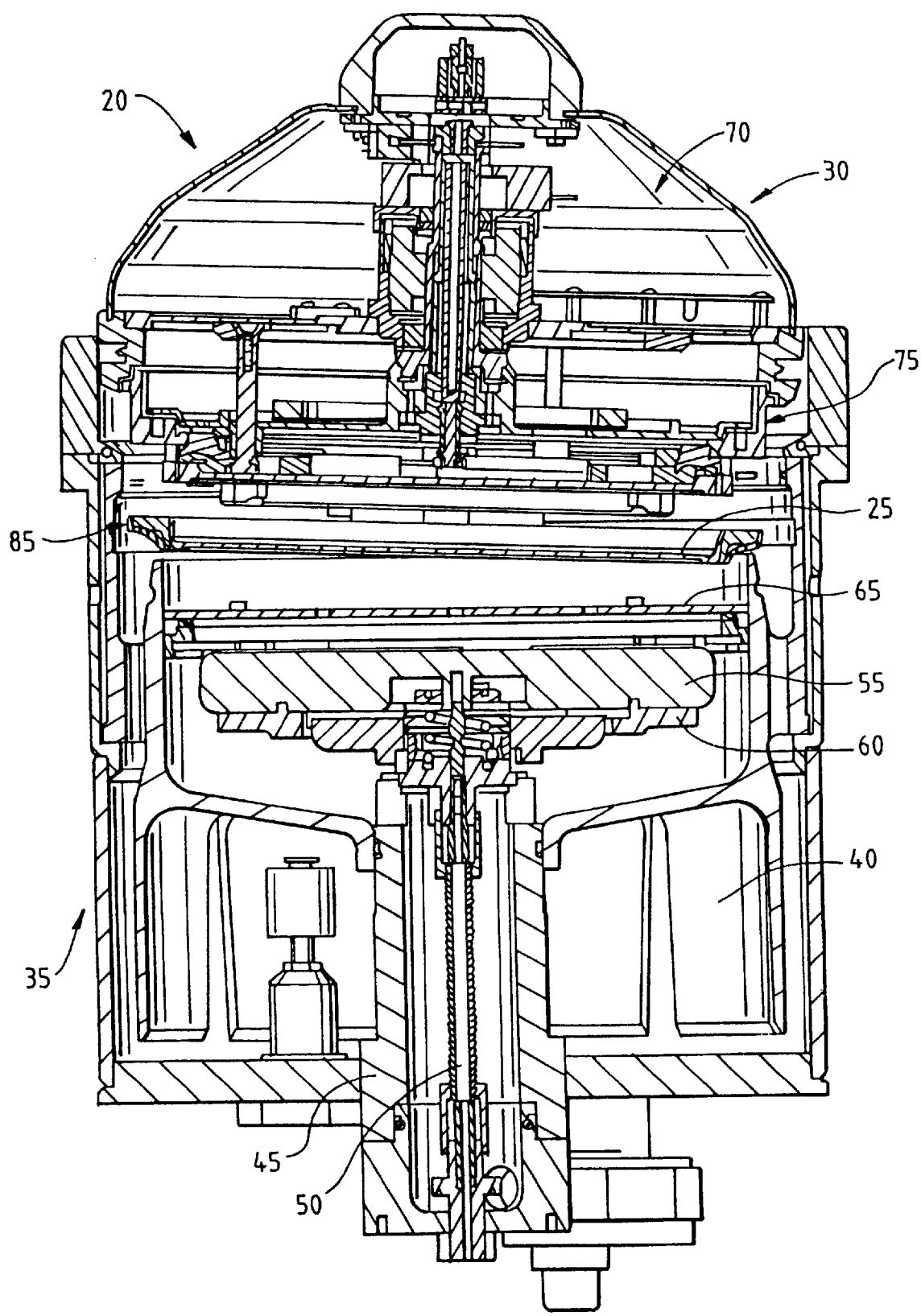
FIG. 1 is a cross-sectional view through an electroplating reactor that is constructed in accordance with various teachings of the present invention.

With reference to FIGS. 1–3, there is shown a reactor assembly 20 for electroplating a microelectronic workpiece, such as a semiconductor wafer 25. Generally stated, the reactor assembly 20 is comprised of a reactor head 30 and a corresponding reactor bowl 35. This type of reactor assembly is particularly suited for effecting electroplating of semiconductor wafers or like workpieces, in which an electrically conductive, thin-film layer of the wafer is electroplated with a blanket or patterned metallic layer.

The specific construction of one embodiment of a reactor bowl 35 suitable for use in the reactor assembly 20 is illustrated in FIG. 2. The electroplating reactor bowl 35 is that portion of the reactor assembly 20 that contains electroplating solution, and that directs the solution against a generally downwardly facing surface of an associated workpiece 25 to be plated. To this end, electroplating solution is circulated through the reactor bowl 35. Attendant to solution circulation, the solution flows from the reactor bowl 35, over the weir-like periphery of the bowl, into a lower overflow chamber 40 of the reactor assembly 20. Solution is drawn from the overflow chamber typically for re-circulation through the reactor.

The reactor bowl 35 includes a riser tube 45, within which an inlet conduit 50 is positioned for introduction of electroplating solution into the reactor bowl 35. The inlet conduit 50 is preferably conductive and makes electrical contact with and supports an electroplating anode 55. The anode 55 may be provided with an anode shield 60. Electroplating solution flows from the inlet conduit 50 through openings at the upper portion thereof, about the anode 55, and through an optional diffusion plate 65 positioned in operative association with the anode. The anode 55 may be consumable whereby metal ions of the anode are transported by the electroplating solution to the electrically-conductive surface of the associated workpiece, which functions as a cathode. Alternatively, the anode 55 may be inert, thereby removing the need for the anode shield 60.

As shown in FIGS. 1 and 3, the reactor head 30 of the electroplating reactor 20 is preferably comprised of a stationary assembly 70 and a rotor assembly 75. Rotor assembly 75 is configured to receive and carry an associated wafer 25 or like workpiece, position the wafer in a process-side down orientation within reactor bowl 35, and to rotate or spin the workpiece while joining its electrically-conductive surface in the plating circuit of the reactor assembly 20. The reactor head 30 is typically mounted on a lift/rotate apparatus 80, which is configured to rotate the reactor head 30 from an upwardly-facing disposition, wherein it receives the wafer to be plated, to a downwardly facing disposition, wherein the surface of the wafer to be plated is positioned downwardly in reactor bowl 35, generally in confronting relationship to diffusion plate 65. A robotic arm 415 (sometimes referred to as including an end effector) is typically employed for placing the wafer 25 in position on the rotor assembly 75, and for removing the plated wafer from within the rotor assembly.

It will be recognized that other reactor assembly configurations may be used with the inventive aspects of the disclosed reactor head, the foregoing being merely illustrative. Another reactor assembly suitable for use in the foregoing configuration is illustrated in U.S. Ser. No. 09/112,300, filed Jul. 9, 1998, and incorporated herein by reference. A still further reactor assembly suitable for use in the foregoing configuration is illustrated in U.S. Ser. No. 60/120,955, filed Apr. 13, 1999, and incorporated herein by reference.

Improved Contact Assemblies

As noted above, the manner in which the electroplating power is supplied to the wafer at the peripheral edge thereof is very important to the overall film quality of the deposited metal. Some of the more desirable characteristics of a contact assembly used to provide such electroplating power include, for example, the following:

uniform distribution of electroplating power about the periphery of the wafer to maximize the uniformity of the deposited film;

consistent contact characteristics to insure wafer-to-wafer uniformity;

minimal intrusion of the contact assembly on the wafer periphery to maximize the available area for device production; and minimal plating on the barrier layer about the wafer periphery to inhibit peeling and/or flaking.

To meet one or more of the foregoing characteristics, reactor 20 preferably employs a ring contact assembly 85 that provides either a continuous electrical contact or a high number of discrete electrical contacts with the wafer 25. By providing a more continuous contact with the outer peripheral edges of the semiconductor wafer 25, in this case around the outer circumference of the semiconductor wafer, a more uniform current is supplied to the semiconductor wafer 25 that promotes more uniform current densities. The more uniform current densities enhance uniformity in the depth of the deposited material.

Contact assembly 85, in accordance with a preferred embodiment, includes contact members that provide minimal intrusion about the wafer periphery while concurrently providing consistent contact with the seed layer. Contact with the seed layer is enhanced by using a contact member structure that provides a wiping action against the seed layer as the wafer is brought into engagement with the contact assembly. This wiping action assists in removing any oxides at the seed layer surface thereby enhancing the electrical contact between the contact structure and the seed layer. As a result, uniformity of the current densities about the wafer periphery are increased and the resulting film is more uniform. Further, such consistency in the electrical contact facilitates greater consistency in the electroplating process from wafer-to-wafer thereby increasing wafer-to-wafer uniformity.

Contact assembly 85, as will be set forth in further detail below, also preferably includes one or more structures that provide a barrier, individually or in cooperation with other structures, that separates the contact/contacts, the peripheral edge portions and backside of the semiconductor wafer 25 from the plating solution. This prevents the plating of metal onto the individual contacts and, further, assists in preventing any exposed portions of the barrier layer near the edge of the semiconductor wafer 25 from being exposed to the electroplating environment. As a result, plating of the barrier layer and the appertaining potential for contamination due to flaking of any loosely adhered electroplated material is substantially limited.

Ring Contact Assemblies Using Flexure Contacts

One embodiment of a contact assembly suitable for use in the assembly 20 is shown generally at 85 of FIGS. 4–10. The contact assembly 85 forms part of the rotor assembly 75 and provides electrical contact between the semiconductor wafer 25 and a source of electroplating power. In the illustrated embodiment, electrical contact between the semiconductor wafer 25 and the contact assembly 85 occurs at a large plurality of discrete flexure contacts 90 that are effectively separated from the electroplating environment interior of the reactor bowl 35 when the semiconductor wafer 25 is held and supported by the rotor assembly 75.

The contact assembly 85 may be comprised of several discrete components. With reference to FIG. 4, when the workpiece that is to be electroplated is a circular semiconductor wafer, the discrete components of the contact assembly 85 join together to form a generally annular component having a bounded central open region 95. It is within this bounded central open region 95 that the surface of the semiconductor wafer that is to be electroplated is exposed. With particular reference to FIG. 6, contact assembly 85 includes an outer body member 100, an annular wedge 105, a plurality of flexure contacts 90, a contact mount member 110, and an interior wafer guide 115. Preferably, annular wedge 105, flexure contacts 90, and contact mount member 110 are formed from platinized titanium while wafer guide 115 and outer body member 100 are formed from a dielectric material that is compatible with the electroplating environment. Annular wedge 105, flexure contacts 90, mount member 110, and wafer guide 115 join together to form a single assembly that is secured together by outer body member 100.

As shown in FIG. 6, contact mount member 110 includes a first annular groove 120 disposed about a peripheral portion thereof and a second annular groove 125 disposed radially inward of the first annular groove 120. The second annular groove 125 opens to a plurality of flexure channels 130 that are equal in number to the number of flexure contacts 90. As can be seen from FIG. 4, a total of 36 flexure contacts 90 are employed, each being spaced from one another by an angle of about 10 degrees.

Referring again to FIG. 6, each flexure contact 90 is comprised of an upstanding portion 135, a transverse portion 140, a vertical transition portion 145, and a wafer contact portion 150. Similarly, wedge 105 includes an upstanding portion 155 and a transverse portion 160. Upstanding portion 155 of wedge 105 and upstanding portion 135 of each flexure contact 90 are secured within the first annular groove 120 of the contact mount member 110 at the site of each flexure channel 130. Self-adjustment of the flexure contacts 90 to their proper position within the overall contact assembly 85 is facilitated by first placing each of the individual flexure contacts 90 in its respective flexure channel 130 so that the upstanding portion 135 is disposed within the first annular groove 120 of the contact mount member 110 while the transition portion 145 and contact portion 150 proceed through the respective flexure channel 130. The upstanding portion 155 of wedge member 105 is then urged into the first annular groove 120. To assist in this engagement, the upper end of upstanding portion 155 is tapered. The combined width of upstanding portion 135 of the flexure contact 90 and upstanding portion 155 of wedge 105 are such that these components are firmly secured with contact mount member 110.

Transverse portion 160 of wedge 105 extends along a portion of the length of transverse portion 140 of each flexure 90. In the illustrated embodiment, transverse portion 160 of wedge portion 105 terminates at the edge of the second annular groove 125 of contact mount member 110. As will be more clear from the description of the flexure contact operation below, the length of transverse portion 160 of wedge 105 can be chosen to provide the desired degree of stiffness of the flexure contacts 90.

Wafer guide 115 is in the form of an annular ring having a plurality of slots 165 through which contact portions 150 of flexures 90 extend. An annular extension 170 proceeds from the exterior wall of wafer guide 115 and engages a corresponding annular groove 175 disposed in the interior wall of contact mount member 110 to thereby secure the wafer guide 115 with the contact mount member 110. As illustrated, the wafer guide member 115 has an interior diameter that decreases from the upper portion thereof to the lower portion thereof proximate contact portions 150. A wafer inserted into contact assembly 85 is thus guided into position with contact portions 150 by a tapered guide wall formed at the interior of wafer guide 115. Preferably, the portion 180 of wafer guide 115 that extends below annular extension 170 is formed as a thin, compliant wall that resiliently deforms to accommodate wafers having different diameters within the tolerance range of a given wafer size. Further, such resilient deformation accommodates a range of wafer insertion tolerances occurring in the components used to bring the wafer into engagement with the contact portions 150 of the flexures 90.

Referring to FIG. 6, outer body member 100 includes an upstanding portion 185, a transverse portion 190, a vertical transition portion 195 and a further transverse portion 200 that terminates in an upturned lip 205. Upstanding portion 185 includes an annular extension 210 that extends radially inward to engage a corresponding annular notch 215 disposed in an exterior wall of contact mount member 110. A V-shaped notch 220 is formed at a lower portion of the upstanding portion 185 and circumvents the outer periphery thereof. The V-shaped notch 220 allows upstanding portion 185 to resiliently deform during assembly. To this end, upstanding portion 185 resiliently deforms as annular extension 210 slides about the exterior of contact mount member 110 to engage annular notch 215. Once so engaged, contact mount member 110 is clamped between annular extension 210 and the interior wall of transverse portion 190 of outer body member 100.

Further transverse portion 200 extends beyond the length of contact portions 150 of the flexure contacts 90 and is dimensioned to resiliently deform as a wafer, such as at 25, is driven against them. V-shaped notch 220 may be dimensioned and positioned to assist in the resilient deformation of transverse portion 200. With the wafer 25 in proper engagement with the contact portions 150, upturned lip 205 engages wafer 25 and assists in providing a barrier between the electroplating solution and the outer peripheral edge and backside of wafer 25, including the flexure contacts 90.

As illustrated in FIG. 6, flexure contacts 90 resiliently deform as the wafer 25 is driven against them. Preferably, contact portions 150 are initially angled upward in the illustrated manner. Thus, as the wafer 25 is urged against contact portions 150, flexures 90 resiliently deform so that contact portions 150 effectively wipe against surface 230 of wafer 25. In the illustrated embodiment, contact portions 150 effectively wipe against surface 230 of wafer 25 a horizontal distance designated at 235. This wiping action assists in removing and/or penetrating any oxides from surface 230 of wafer 25 thereby providing more effective electrical contact between flexure contacts 90 and the seed layer at surface 230 of wafer 25.

With reference to FIGS. 7 and 8, contact mount member 110 is provided with one or more ports 240 that may be connected to a source of purging gas, such as a source of nitrogen. As shown in FIG. 8, purge ports 240 open to second annular groove 125 which, in turn, operates as a manifold to distribute the purging gas to all of the flexure channels 130 as shown in FIG. 6. The purging gas then proceeds through each of the flexure channels 130 and slots 165 to substantially surround the entire contact portions 150 of flexures 90. In addition to purging the area surrounding contact portions 150, the purge gas cooperates with the upturned lip 205 of outer body member 100 to effect a barrier to the electroplating solution. Further circulation of the purge gas is facilitated by an annular channel 250 formed between a portion of the exterior wall of wafer guide 115 and a portion of the interior wall of contact mount member 110.

As shown in FIGS. 4, 5 and 10, contact mount member 110 is provided with one or more threaded apertures 255 that are dimensioned to accommodate a corresponding connection plug 260. With reference to FIGS. 5 and 10, connection plugs 260 provide electroplating power to the contact assembly 85 and, preferably, are each formed from platinized titanium. In a preferred form of plugs 260, each plug 260 includes a body 265 having a centrally disposed bore hole 270. A first flange 275 is disposed at an upper portion of body 265 and a second flange 280 is disposed at a lower portion of body 265. A threaded extension 285 proceeds downward from a central portion of flange 280 and secures with threaded bore hole 270. The lower surface of flange 280 directly abuts an upper surface of contact mount member 110 to increase the integrity of the electrical connection therebetween.

Although flexure contacts 90 are formed as discrete components, they may be joined with one another as an integral assembly. To this end, for example, the upstanding portions 135 of the flexure contacts 90 may be joined to one another by a web of material, such as platinized titanium, that is either formed as a separate piece or is otherwise formed with the flexures from a single piece of material. The web of material may be formed between all of the flexure contacts or between select groups of flexure contacts. For example, a first web of material may be used to join half of the flexure contacts (e.g., 18 flexure contacts in the illustrated embodiment) while a second web of material is used to join a second half of the flexure contacts (e.g., the remaining 18 flexure contacts in the illustrated embodiment). Different groupings are also possible.

A further embodiment of a contact assembly employing flexure contacts such as those described above is illustrated in FIGS. 11–15. As illustrated in FIG. 11, contact assembly 85b is again adapted to accommodate a semiconductor wafer and is in many respects similar to contact assembly 85 of FIGS. 4–10. Accordingly, components in contact assembly 85b are referenced using the same reference numbers associated with contact assembly 85, except that the components of contact assembly 85b include a "b" suffix.

In this embodiment, with reference to FIG. 15, an outer body member 100b is formed from a plastic material or the like that is electrically non-conductive and is chemically compatible with the electroplating environment. The outer body member 100b is provided with an annular groove 290b into which is provided an O-ring 295b. As will be explained in further detail below, the O-ring 295b seals against face 230b of the semiconductor wafer 25 to assist in preventing contact between the flexure contacts 90b and the electroplating environment within the reactor bowl 35.

The contact assembly 85b also includes an annular stiffening ring 300b, a contact mount member 110b, and a plurality of flexure contacts 90b. Contact mount member 110b is in the form of an annular ring having a plurality of slots 165b through which contact portions 150b of flexures 90b extend. As illustrated the contact mount member has an interior diameter distal contact portions 150b that is greater than the interior diameter proximate contact portions 150b. A wafer inserted into the contact assembly 85b is thus guided into position with contact portions 150b by a tapered guide wall formed at the interior of contact mount member 110b.

As above the flexure contacts 90 of the illustrated embodiment are formed as discrete components each having an upstanding portion 135b, a transverse portion 140b, a vertical transition portion 145b, and a contact portion 150b. The contact portions 150b protrude through respective ones of the plurality of slots 165b.

Integration of the foregoing components to form the contact assembly 85b, as well as the operation of the contact assembly, is best understood with reference again to FIG. 15. In the illustrated embodiment, the various components are clamped together by the outer body member 100b. As illustrated, contact mount member 110b and outer body member 100b define a plurality of flexure chambers, shown generally at 130b. Each flexure chamber includes an upwardly extending portion 120b that is defined on each side by chamferred members 300b that extend radially outward from the inner body member 110b. The chamferred members 300b are designed to be engaged by nose portion 210b of the outer body member 100b through a camming action whereby nose portion 210b clamps the contact mount member 110b, transverse portions 140b of flexures 90b and annular stiffening ring 300b against a laterally extending portion 190b of the outer body member 100b. Depending on the material from which the outer body member 100b is formed, it may be desirable to include a notch 220b in the outer body member 100b to facilitate the camming action of the nose portion 215b over the one or more chamferred members 160 and, if desired, resilient deformation of the outer body member 100b when wafer 25 is urged into operative relationship with the overall contact assembly 85b.

Optionally, a non-reactive gas, such as nitrogen, can be used to purge the flexure contacts 90b and the back side of wafer 25. To this end, the wafer guide 115b may be provided with one or more purge ports 240b that serve to provide fluid communication of a purging gas to an annular manifold 125b and, therefrom, through the flexure chambers 130b so as to substantially surround contact portions 150b. The purge gas then flows through openings 165b to the peripheral edge of the semiconductor wafer 25 and to backside of the semiconductor wafer. Such measures enhance the isolation of the flexure contacts 90b and the backside of the semiconductor wafer 25 from the processing environment.

In operation, the semiconductor wafer 25 is driven against the flexure contacts 90b so that a face 230b of the semiconductor wafer 25 is sealed against the O-ring and corresponding portion of the outer body member 100b. When driven in this manner, each flexure contact 90 is driven a vertical distance and a horizontal distance 235b. This movement causes the flexure contacts 90b to wipe against the side 230b of the semiconductor wafer 25 thereby assisting in the removal or penetration of, for example, seed layer oxides or the like and enhancing electrical contact between the flexure contacts 90b and the semiconductor wafer 25. The amount of deflection and bias can be altered as a function of the radial width of the annular stiffening ring 300b. A large deflection can be used to accommodate large manufacturing tolerance variations while still providing proper electrical contact as well as sealing of the contact assembly 85 against the semiconductor wafer 25.

In the embodiment of contact assembly 85b, the axial force applied to the semiconductor wafer 25 is divided between the force required to deflect the flexure contacts 90 and that required to energize the seal. This provides a load path that is independent of the structure, which contains the seal thereby isolating deflection of the contacts from dependency on the deflection of the O-ring 105 to form the seal.

Belleville Ring Contact Assemblies

Alternative contact assemblies are illustrated in FIGS. 16–25. In each of these contact assemblies, the contact members are integrated with a corresponding common ring and, when mounted in their corresponding assemblies, are biased upward in the direction in which the wafer or other substrate is received upon the contact members. A top view of one embodiment of such a structure is illustrated in FIG. 16A while a perspective view thereof is illustrated in FIG. 16B. As illustrated, a ring contact, shown generally at 610, is comprised of a common ring portion 630 that joins a plurality of contact members 655. The common ring portion 630 and the contact members 655, when mounted in the corresponding assemblies, are similar in appearance to half of a conventional Belleville spring. For this reason, the ring contact 610 will be hereinafter referred to as a "Bellville ring contact" and the overall contact assembly into which it is placed will be referred to as a "Bellville ring contact assembly".

Figure 16A:
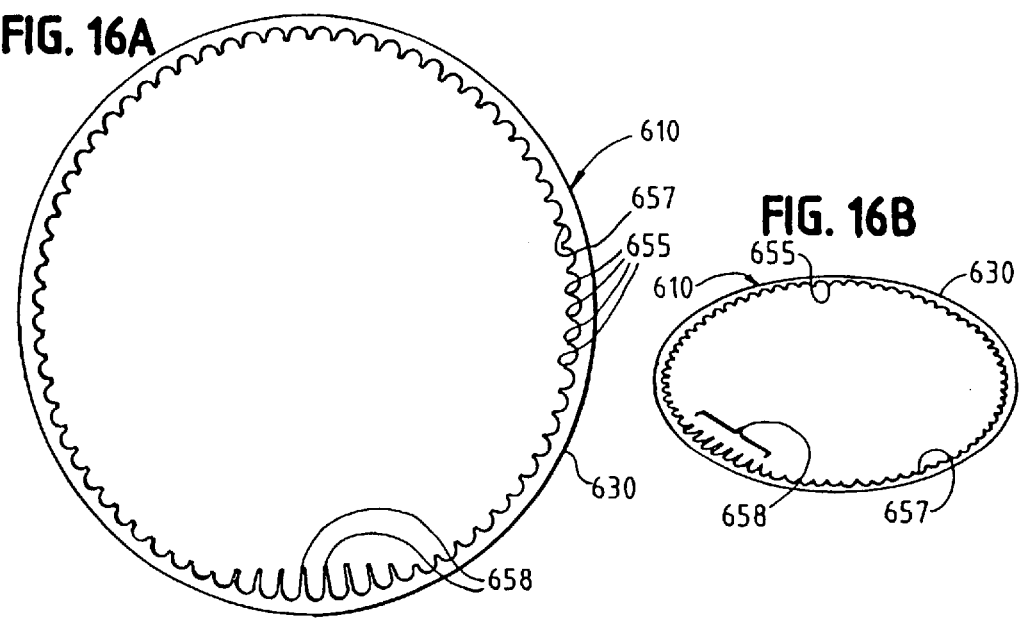
FIGS. 16A and B–17 illustrate two different embodiments of a "Belleville ring" contact structure.
Figure 16B:
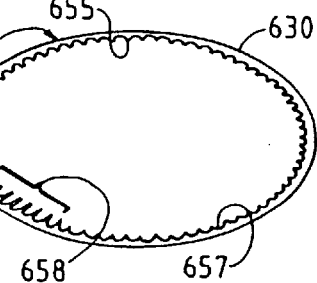

The embodiment of Belleville ring contact 610 illustrated in FIGS. 16A and 16B includes 72 contact members 655 and is preferably in formed from platinized titanium. The contact members 655 may be formed by cutting arcuate sections 657 into the interior diameter of a platinized titanium ring. A predetermined number of the contact members 658 have a greater length than the remaining contact members 655 to, for example, accommodate certain flat-sided wafers.

Figure 17:
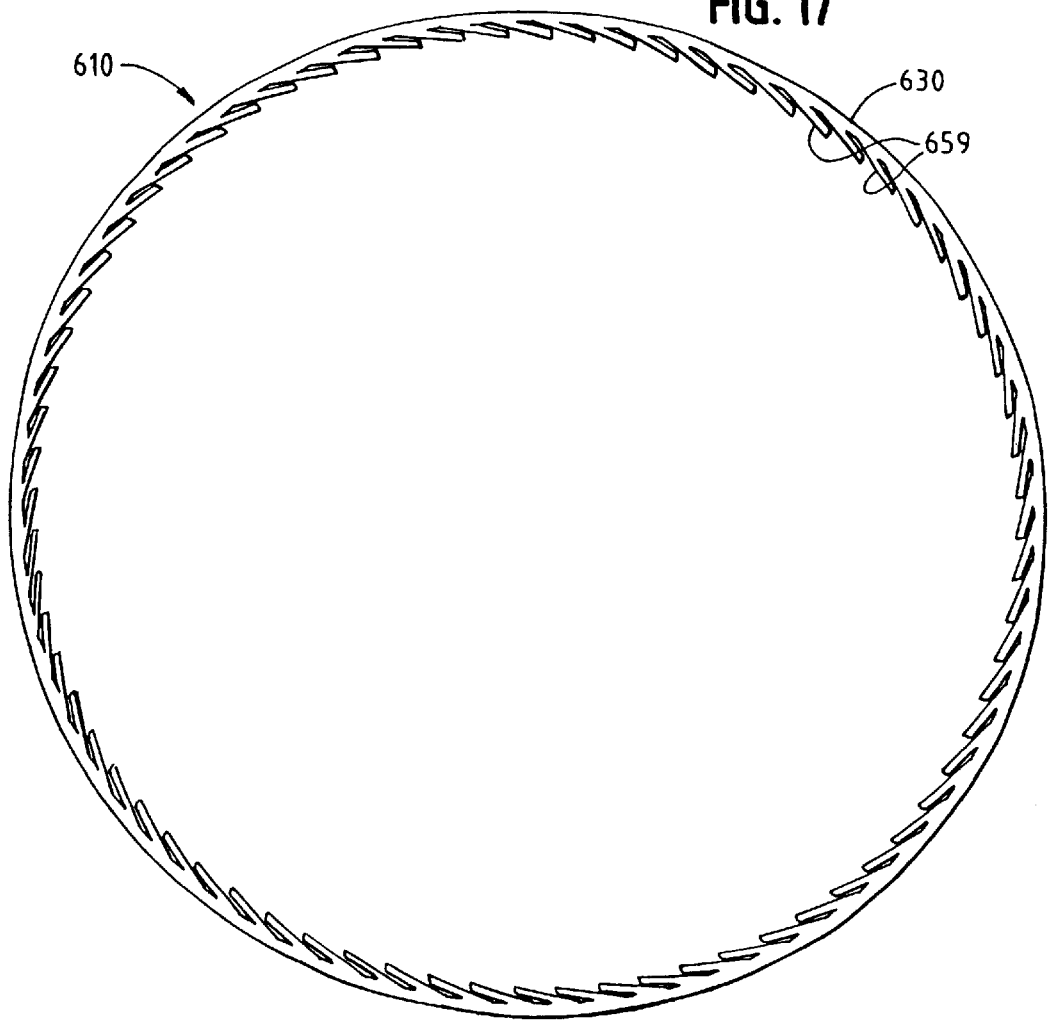

A further embodiment of a Belleville ring contact 610 is illustrated in FIG. 17. As above, this embodiment is preferably formed from platinized titanium. Unlike the embodiment of FIGS. 16A and 16B in which all of the contact members 655 extend radially inward toward the center of the structure, this embodiment includes contact members 659 that are disposed at an angle. This embodiment constitutes a single-piece design that is easy to manufacture and that provides a more compliant contact than does the embodiment of FIGS. 16A and 16B with the same footprint. This contact embodiment can be fixtured into the "Belleville" form in the contact assembly and does not require permanent forming. If the Belleville ring contact 610 of this embodiment is fixtured in place, a complete circumferential structure is not required. Rather the contact may be formed and installed in segments thereby enabling independent control/sensing of the electrical properties of the segments.

A first embodiment of a Bellville ring contact assembly is illustrated generally at 600 in in FIGS. 18–20. As illustrated, the contact assembly 600 comprises a conductive contact mount member 605, a Bellville ring contact 610, a dielectric wafer guide ring 615, and an outer body member 625. The outer, common portion 630 of the Bellville ring contact 610 includes a first side that is engaged within a notch 675 of the conductive base ring 605. In many respects, the Belleville ring contact assembly of this embodiment is similar in construction with the flexure contact assembly 85 described above. For that reason, the functionality of many of the structures of the contact assembly 600 will be apparent and will not be repeated here.

Preferably, the wafer guide ring 615 is formed from a dielectric material while contact mount member 605 is formed from a single, integral piece of conductive material or from a dielectric or other material that is coated with a conductive material at its exterior. Even more preferably, the conductive ring 605 and Bellville ring contact 610 are formed from platinized titanium or are otherwise coated with a layer of platinum.

The wafer guide ring 615 is dimensioned to fit within the interior diameter of the contact mount member 605. Wafer guide ring 615 has substantially the same structure as wafer guides 115 and 115b described above in connection with contact assemblies 85 and 85b, respectively. Preferably, the wafer guide ring 615 includes an annular extension 645 about its periphery that engages a corresponding annular slot 650 of the conductive base ring 605 to allow the wafer guide ring 615 and the contact mount member 605 to snap together.

The outer body member 625 includes an upstanding portion 627, a transverse portion 629, a vertical transition portion 632 and a further transverse portion 725 that extends radially and terminates at an upturned lip 730. Upturned lip 730 assists in forming a barrier to the electroplating environment when it engages the surface of the side of workpiece 25 that is being processed. In the illustrated embodiment, the engagement between the lip 730 and the surface of workpiece 25 is the only mechanical seal that is formed to protect the Bellville ring contact 610.

The area proximate the contacts 655 of the Belleville ring contact 610 is preferably purged with an inert fluid, such as nitrogen gas, which cooperates with lip 730 to effect a barrier between the Bellville ring contact 610, peripheral portions and the backside of wafer 25, and the electroplating environment. As particularly shown set forth in FIGS. 19 and 20, the outer body member 625 and contact mount member 605 are spaced from one another to form an annular cavity 765. The annular cavity 765 is provided with an inert fluid, such as nitrogen, through one or more purge ports 770 disposed through the contact mount member 605. The purged ports 770 open to the annular cavity 765, which functions as a manifold to distribute to the inert gas about the periphery of the contact assembly. A given number of slots, such as at 780, corresponding to the number of contact members 655 are provided and form passages that route the inert fluid from the annular cavity 765 to the area proximate contact members 655.

FIGS. 19 and 20 also illustrate the flow of a purging fluid in this embodiment of Bellville ring contact assembly. As illustrated by arrows, the purge gas enters purge port 770 and is distributed about the circumference of the assembly 600 within annular cavity 765. The purged gas then flows through slots 780 and below the lower end of contact mount member 605 to the area proximate Bellville contact 610. At this point, the gas flows to substantially surround the contact members 655 and, further, may proceed above the periphery of the wafer to the backside thereof. The purging gas may also proceed through an annular channel 712 defined by the contact mount member 605 and the interior of the compliant wall formed at the lower portion of wafer guide ring 615. Additionally, the gas flow about contact members 655 cooperates with upturned lip 730 effect a barrier at lip 730 that prevents electroplating solution from proceeding therethrough.

When a wafer or other workpiece 25 is urged into engagement with the contact assembly 600, the workpiece 25 first makes contact with the contact members 655. As the workpiece is urged further into position, the contact members 655 deflect and effectively wipe the surface of workpiece 25 until the workpiece 25 is pressed against the upturned lip 730. This mechanical engagement, along with the flow of purging gas, effectively isolates the outer periphery and backside of the workpiece 25 as well as the Bellville ring contact 610 from contact with the plating solution.

Figure 22:
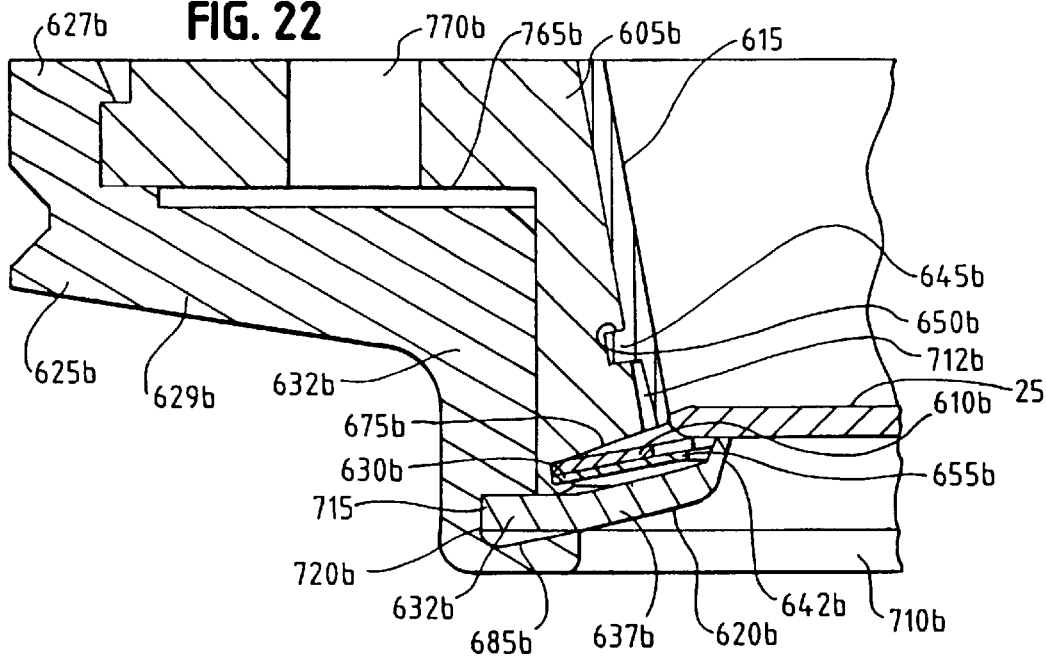
Figure 23:
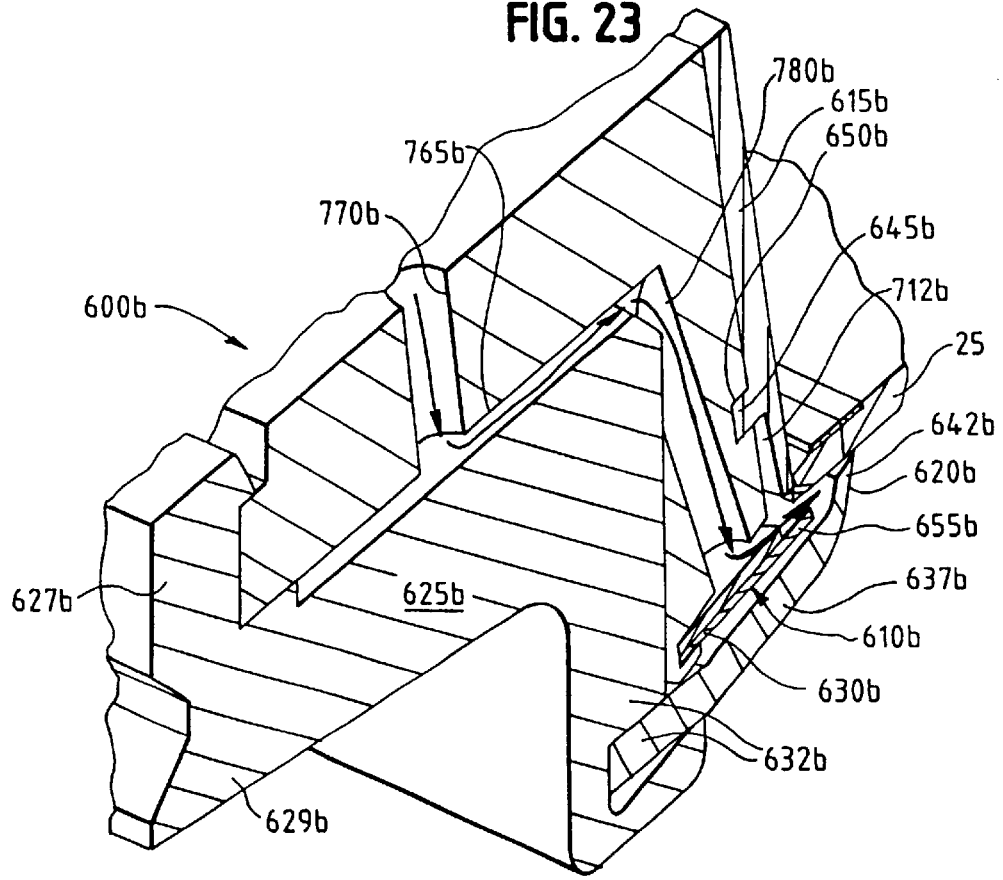

A further embodiment of a Bellville ring contact assembly is shown generally at 600b of FIGS. 21–23. In this embodiment, a separate barrier member 620b is employed. In most other respects, Bellville ring contact assembly 600b is substantially similar to Bellville ring contact assembly 600 above. Accordingly, similar components of assembly 600b are labeled with the same reference numbers as assembly 600 above, except that the similar components of assembly 600b include a "b" suffix.

As particularly illustrated in FIG. 22, barrier member 620b includes a transverse section 632b, an angled section 637b and an upturned lip 642b. Transverse section 632b of barrier member 620b is disposed in an annular groove 720b disposed in the outer body member 625b. Annular groove 720b is defined at its lower end by a transverse extending flange 710b having an angled wall 685b that contacts the barrier member 620b at the end of transverse section 632b that meets the angled section 637b. This assists in stiffening the barrier member 620b to insure proper engagement with the lower face of wafer 25.

Like assembly 600, assembly 600b is preferably adapted to distribute a purging gas therethrough. FIG. 23 illustrates one manner in which a flow of the purging gas can be provided through Bellville ring contact assembly 600b. As illustrated, outer body member 625b and contact mount member 605b join to define the requisite flow passages.

With particular reference to FIG. 22, the contact members 655b of the Bellville ring contact 610b protrude beyond the barrier member 620b. When a wafer or other workpiece 25 is urged into engagement with the contact assembly 600b, the workpiece 25 first makes contact with the contact members 655b. As the workpiece is urged further, the contact members 655b deflect and effectively wipe the surface of workpiece 25 until the workpiece 25 is pressed against the barrier member 620b. This mechanical engagement, along with the flow of purging gas, effectively isolates the outer periphery and backside of the workpiece 25 as well as the Bellville ring contact 610b from contacting the plating solution.

Figure 24:
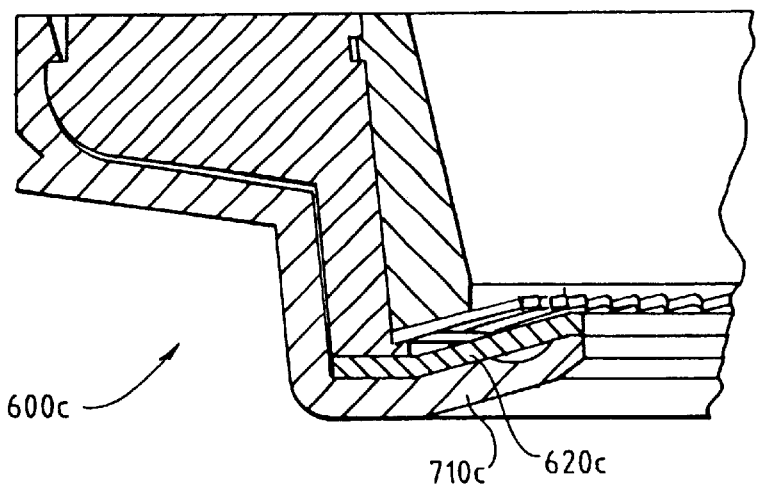
FIG. 24 illustrates another embodiment of a contact assembly using a "Belleville ring" contact structure, such as one of those illustrated in FIGS. 15–17, that is suitable for use in the reactor assembly illustrated in FIG. 1.

Another embodiment of a Bellville ring contact assembly is shown generally at 600c of FIG. 24. This embodiment is substantially similar to contact assembly 600b and, as such, similar reference generals are used to designate similar parts, except that the components of contact assembly 600c include a "c" suffix.

The principal difference between contact assembly 600c and 600b can best be understood with reference to a comparison between FIG. 22 and FIG. 24. As illustrated, the principal difference relates to the shape of the flange 710c and the elastomeric seal member 620c. In the embodiment of contact assembly 600c, the flange 710c and elastomeric seal member 620c are co-extensive with one another. As such, the seal against the bottom surface of the wafer 25 is not as compliant. Nevertheless, this structure abuts the bottom of the wafer to effectively form a barrier against the plating solution, particularly when used in conjunction with a purging gas.

Figure 25:
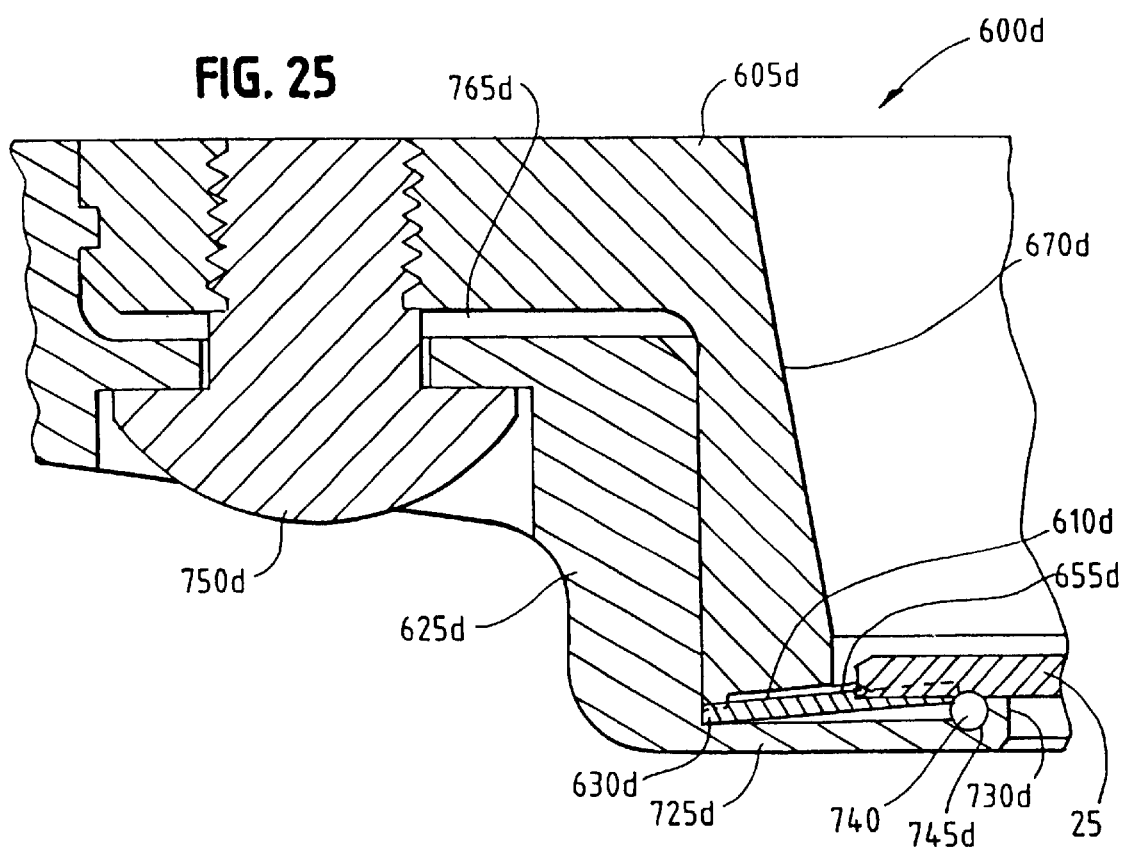
FIG. 25 illustrates a still further embodiment of a contact assembly using a "Belleville ring" contact structure, such as one of those illustrated in FIGS. 15–17, that is suitable for use in the assembly illustrated in FIG. 1.

A cross-sectional view of a still further embodiment of a Bellville ring contact assembly is a shown generally at 600d of FIG. 25. In this embodiment, an O-ring 740 is disposed in a corresponding notch 745 of the outer body member 625d to form a sealing arrangement against the surface of workpiece 25 when the workpiece is urged against the contacts 655d Bellville ring contact 610d. The O-ring 740d is dimensioned to protrude beyond lip 730d of the outer body member 625d. Lip 730d of the outer body member 625d thereby assists in backing-up the O-ring seal.

Bellville ring contact assembly 600d, unlike the other contact assemblies described above, does not necessarily include a wafer guide ring. Rather, assembly 600d illustrates the use of one or more securements 750 that are used to fasten the various components to one another and the interior wall of contact mount member 605d is slanted to provide the wafer guide surface.

Other Contact Assemblies

FIGS. 26 and 27 illustrate further embodiments of plating contacts and peripheral seal members. With reference to FIG. 26, the arrangement includes the plating contact, which is provided in the form of an annular contact member or ring 834 for mounting on the rotor assembly of the electroplating apparatus. While the annular contact ring is illustrated as being circular in configuration, it will be understood that the annular contact ring can be non-circular in configuration. An annular seal member 836 is provided in operative association with the annular contact ring, and as will be further described, cooperates with the contact ring to provide continuous sealing of a peripheral region of the workpiece which is positioned in electrically-conductive contact with the annular contact ring.

The annular contact ring 834 includes a mounting portion 838 by which the contact ring is mounted for rotation on the rotor assembly of the electroplating apparatus. The contact ring is also electrically joined with suitable circuitry provided in the rotor assembly, whereby the contact ring is electrically joined in the circuitry of the electroplating apparatus for creating the necessary electrical potential at the surface of the wafer 25 (the cathode) for effecting electroplating. The annular contact ring further includes a depending support portion 840, and an annular contact portion 842 which extends inwardly of the mounting portion 838. The annular contact portion 842 defines a generally upwardly facing contact surface 844 which is engaged by the wafer 25 to establish electrical contact between the contact ring and the seed layer of the wafer. It is contemplated that the annular contact portion 842 of the contact ring provide substantially continuous electrically-conductive contact with a peripheral region of the associated wafer or other workpiece.

The annular contact ring 834 is preferably configured to promote centering of workpiece 25 on the contact ring and its associated seal member. The contact ring preferably includes an inwardly facing conic guide surface 835 for guiding the workpiece into centered (i.e., concentric) relationship with the contact ring and associated seal member. The conic guide surface 835 acts as an angled lead-in (preferably angled between about 2 degrees and 15 degrees from vertical) on the contact ring inner diameter to precisely position the outside diameter of the workpiece on the contact diameter (i.e., ensure that workpiece is as concentric as possible on the contact ring). This is important for minimizing the overlap of the contact and its associated seal onto the surface of the workpiece, which can be quite valuable if it comprises a semiconductor wafer.

The annular seal member 836 of the present construction is positioned in operative association with the annular contact ring 834, whereby a peripheral region of the wafer 25 is sealed from electroplating solution in the electroplating apparatus. The wafer 25 can be held in position for electrical contact with the annular contact ring 834 by an associated backing member 846, with disposition of the wafer in this fashion acting to position the wafer in resilient sealing engagement with the peripheral seal member 36.

The peripheral seal member 836 is preferably formed from polymeric or elastomeric material, preferably a fluoroelastomer such as AFLAS, available from the 3M Company. The seal member 836 preferably includes a portion having a substantially J-shaped cross-sectional configuration. In particular, the seal member 836 includes a generally cylindrical mounting portion 848 which fits generally about support portion 840 of annular contact ring 34, and may include a skirt portion 49 which fits generally about mounting portion 38 of the contact ring. The seal member further includes a generally inwardly extending, resiliently deformable seal lip 850, with the mounting portion 838 of the seal lip 850 together providing the portion of the seal member having a J-shaped cross-sectional configuration. As illustrated in FIG. 26, the annular seal lip 850 initially projects beyond the contact portion 842 of the annular contact ring in a direction toward the wafer 25 or other workpiece. As a result, the deformable seal lip is resiliently biased into continuous sealing engagement with the peripheral region of the wafer when the wafer is positioned in electrically-conductive contact with the contact portion of the contact ring.

In the embodiment of the present invention illustrated in FIG. 26, the annular seal lip 850 has an inside dimension (i.e., inside diameter) less than an inside dimension (i.e., inside diameter) of the contact portion 842 of the annular contact ring 834. By this arrangement, the seal lip 850 engages the wafer radially inwardly of the contact portion 842, to thereby isolate the contact portion from plating solution in the electroplating apparatus. This arrangement is preferred when it is not only desirable to isolate a peripheral region of the wafer or other workpiece from the electroplating solution, but to also isolate the annular contact ring from the solution, thereby minimizing deposition of metal on the annular contact ring during electroplating.

The seal member 836 is preferably releaseably retained in position on the annular contact ring 834. To this end, at least one retention projection is provided on one of the seal member and contact ring, with the other of the seal member and contact ring defining at least one recess for releaseably retaining the retention projection. In the illustrated embodiment, the seal member 836 is provided with a continuous, annular retention projection 852, which fits within an annular recess 854 defined by annular contact ring 834. The polymeric or elastomeric material from which the seal member 836 is preferably formed promotes convenient assembly of the seal member onto the contact ring by disposition of the projection 852 in the recess 854.

FIG. 27 illustrates an annular contact ring 934 embodying the principles of the present invention, including a mounting portion 938, a depending support portion 940, and an inwardly extending annular contact portion 942, having a contact surface 944 configured for electrically-conductive contact with a peripheral region of an associated wafer 25 or other workpiece. This embodiment differs from the previously-described embodiment, in that the associated peripheral seal member, designated 936, including a seal lip that engages the workpiece outwardly (rather than inwardly of) the associated annular contact ring.

The annular seal member 934 has a generally J-shaped cross-sectional configuration, and includes a generally cylindrical mounting portion 948, and a resiliently deformable annular seal lip 950 which extends radially inwardly of the mounting portion. As in the previous embodiment, the deformable seal lip 950 initially projects beyond the contact portion 942 in a direction toward the wafer 25, so that the seal lip 950 is resiliently biased into continuous engagement with the peripheral region of the wafer when the wafer is positioned in electrically-conductive contact with the contact portion 942 of the contact ring 934. In this embodiment, the seal ring 950 has an inside dimension (i.e., inside diameter) greater than the inside dimension (i.e., inside diameter) of the annular contact portion 942. By this arrangement, the annular contact portion engages the workpiece radially inwardly of the seal lip. Attendant to positioning of the wafer 25 in electrically-conductive contact with the annular contact portion 942, the deformable seal lip 950 of the peripheral seal member is deformed generally axially of the cylindrical mounting portion 948 thereof. The seal member is thus maintained in sealing contact with the peripheral portion of the wafer, whereby edge and rear surfaces of the wafer are isolated from plating solution within the electroplating apparatus.

As in the previous embodiment, the peripheral seal member 936 is configured for releasable retention generally within the annular contact ring 934. To this end, the annular seal member 936 includes a continuous annular retention projection 952 which is releaseably retained within a continuous annular recess 954 defined by the annular contact ring 934. This arrangement promotes efficient assembly of the seal member and contact ring.

Rotor Contact Connection Assembly

In many instances, it may be desirable to have a given reactor assembly 20 function to execute a wide range of electroplating recipes. Execution of a wide range of electroplating and electroless plating recipes may be difficult, however, if the process designer is limited to using a single contact assembly construction. Further, the plating contacts used in a given contact assembly construction must be frequently inspected and, sometimes, replaced. This is often difficult to do in existing electroplating reactor tools, frequently involving numerous operations to remove and/or inspect the contact assembly. The present inventor has recognized this problem and has addressed it by providing a mechanism by which the contact assembly 85 is readily attached and detached from the other components of the rotor assembly 75. Further, a given contact assembly type can be replaced with the same contact assembly type without recalibration or readjustment of the system.

To be viable for operation in a manufacturing environment, such a mechanism should accomplish several functions including:

1. Provide secure, fail-safe mechanical attachment of the contact assembly to other portions of the rotor assembly;
2. Provide electrical interconnection between the contacts of the contact assembly and a source of electroplating power;
3. Provide a seal at the electrical interconnect interface to protect against the processing environment (e.g., wet chemical environment);
4. Provide a sealed path for purge the asked to the contact assembly; and
5. Minimize use of tools or fasteners which can be lost, misplaced, or used in a manner that damages the electroplating equipment.

Figure 28:
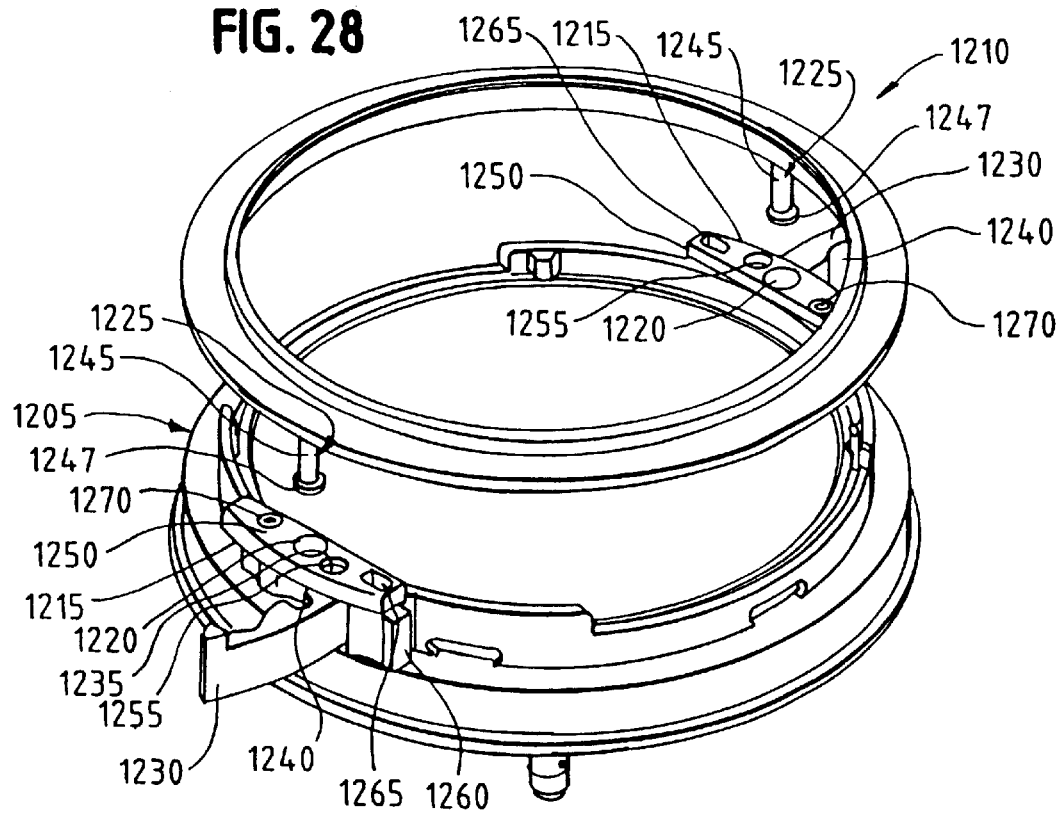
FIGS. 28, 29, 30A & B, 31A, B and C, and 32A–D illustrate various aspects of one embodiment of a quick-attach mechanism.
Figure 29:
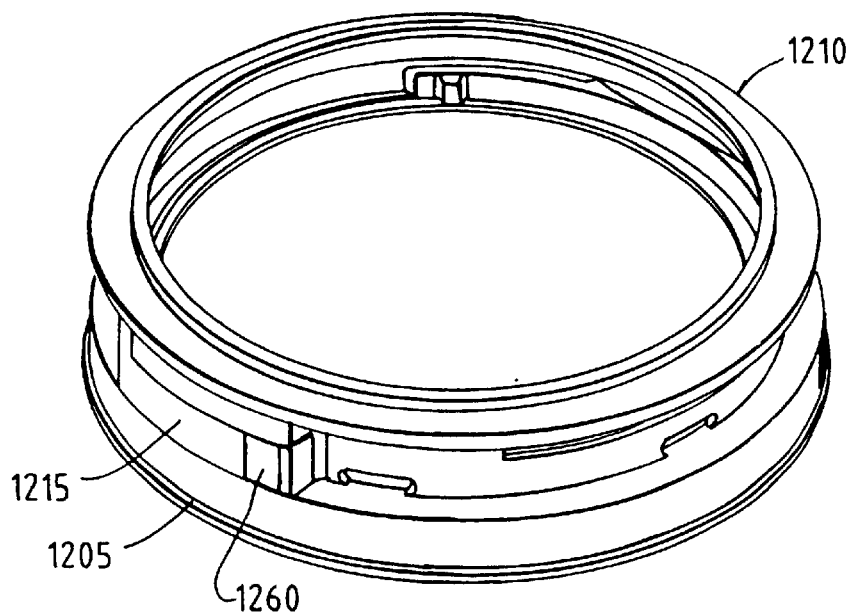

FIGS. 28 and 29 illustrate one embodiment of a quick-attach mechanism that meets the foregoing requirements. For simplicity, only those portions of the rotor assembly 75 necessary to understanding the various aspects of the quick-attach mechanism are illustrated in these figures.

As illustrated, the rotor assembly 75 may be comprised of a rotor base member 205 and a removable contact assembly 1210. Preferably, the removable contact assembly 1210 is constructed in one of the manners set forth above. The illustrated embodiment, however, employs a continuous ring contact, such as shown in FIG. 26.

The rotor base member 1205 is preferably annular in shape to match the shape of the semiconductor wafer 25. A pair of latching mechanisms 1215 are disposed at opposite sides of the rotor base member 1205. Each of the latching mechanisms 1215 includes an aperture 1220 disposed through an upper portion thereof that is dimensioned to receive a corresponding electrically conductive shaft 1225 that extends downward from the removable contact assembly 1210.

The removable contact assembly 210 is shown in a detached state in FIG. 28. To secure the removable contact assembly 1210 to the rotor base member 1205, an operator aligns the electrically conductive shafts 1225 with the corresponding apertures 1220 of the latching mechanisms 1215. With the shafts 1225 aligned in this manner, the operator urges the removable contact assembly 1210 toward the rotor base member 1205 so that the shafts 1225 engage the corresponding apertures 1220. Once the removable contact assembly 1210 is placed on the rotor base member 1205, latch arms 1230 are pivoted about a latch arm axis 1235 so that latch arm channels 1240 of the latch arms 1230 engage the shaft portions 1245 of the conductive shafts 1235 while concurrently applying a downward pressure against flange portions 1247. This downward pressure secures the removable contact assembly 1210 with the rotor base member 1205. Additionally, as will be explained in further detail below, this engagement results in the creation of an electrically conductive path between electrically conductive portions of the rotor base assembly 1205 and the electroplating contacts of the contact assembly 1210. It is through this path that the electroplating contacts of the contact assembly 1210 are connected to receive power from a plating power supply.

Figure 30A:
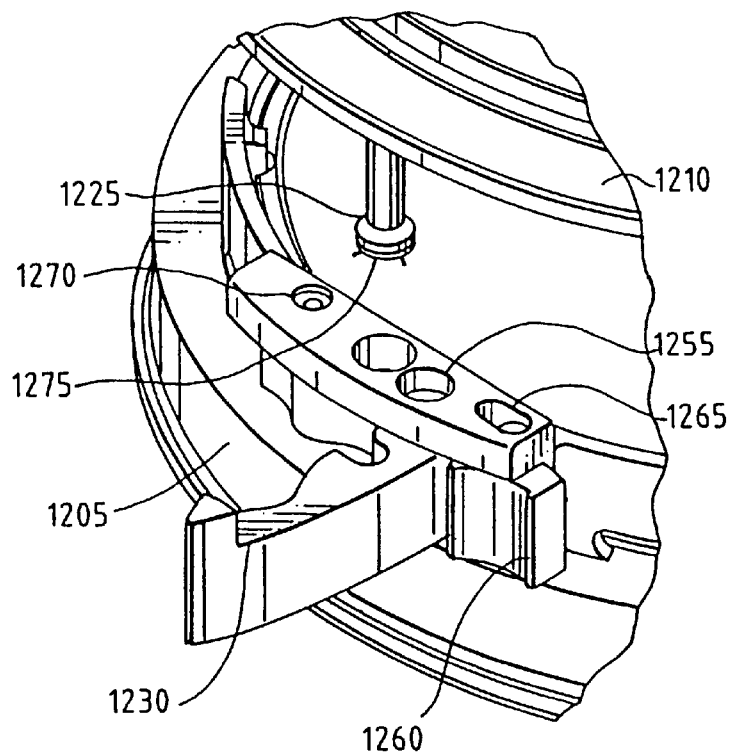
Figure 30B:
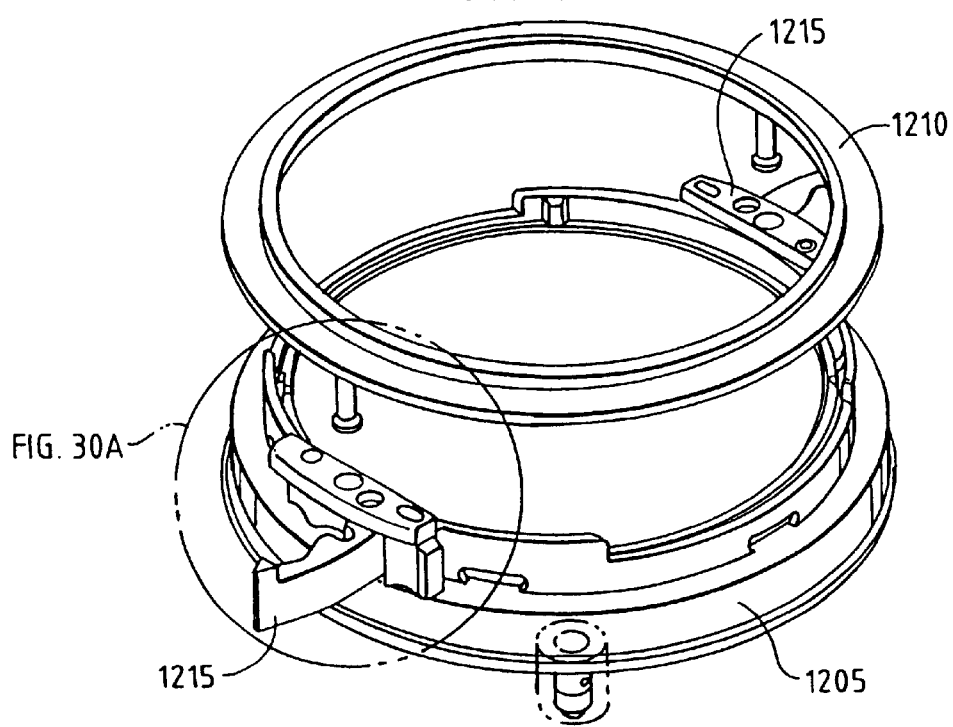

FIGS. 30A and 30B illustrate further details of the latching mechanisms 1215 and the electrically conductive shafts 1225. As illustrated, each latching mechanism 1215 is comprised of a latch body 1250 having aperture 1220, a latch arm 1230 disposed for pivotal movement about a latch arm pivot post 1255, and a safety latch 1260 secured for relatively minor pivotal movement about a safety latch pivot post 1265. The latch body 1250 may also have a purge port 270 disposed therein to conduct a flow of purging fluid through corresponding apertures of the removable contact assembly 1210. An O-ring 1275 is disposed at the bottom of the flange portions of the conductive shafts 1225.

Figure 31A:
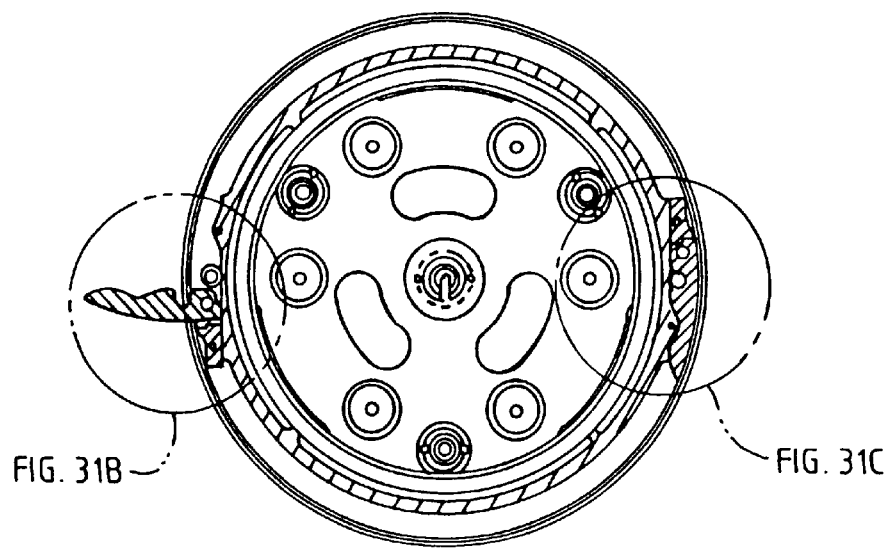
Figure 31B:
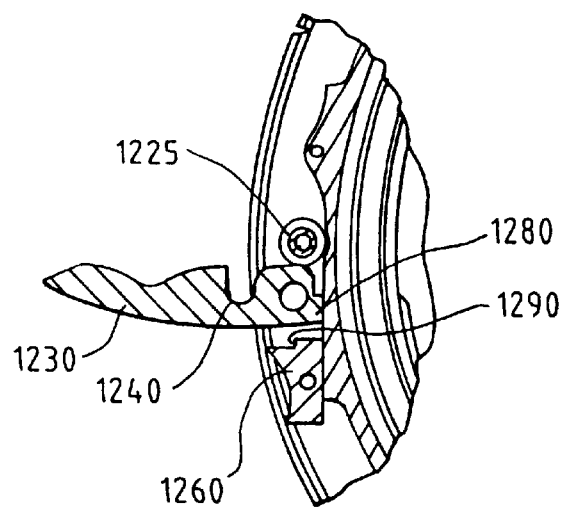
Figure 31C:
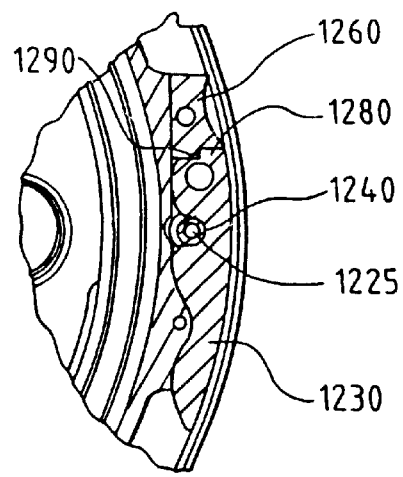
Figure 32A:
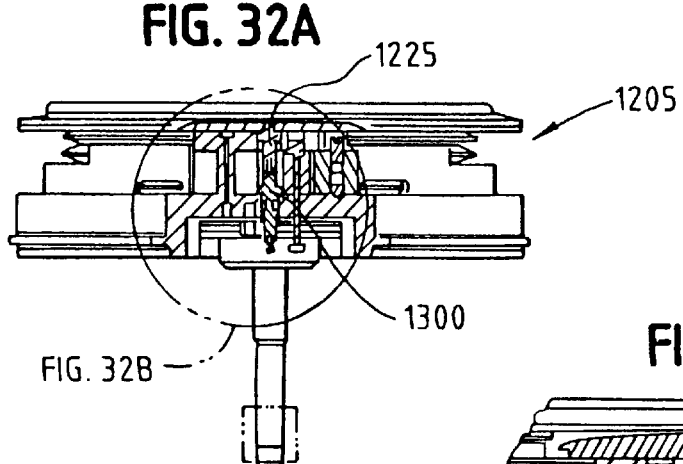
Figure 32B:
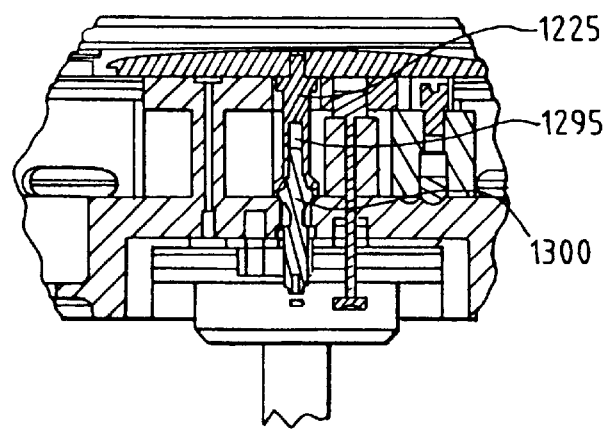
Figure 32C:
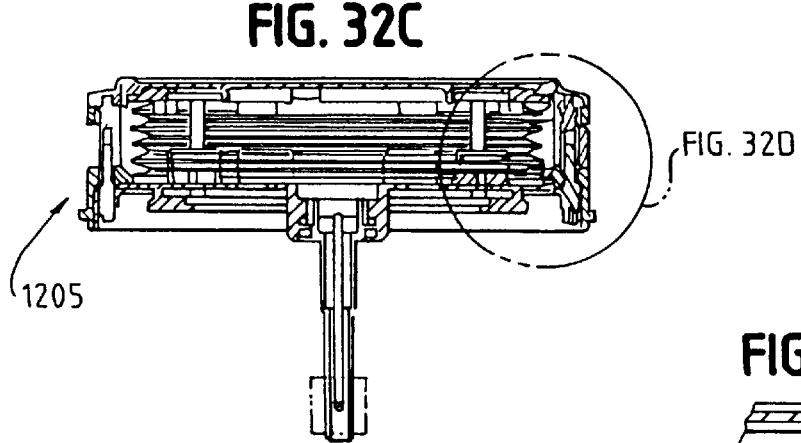
Figure 32D:
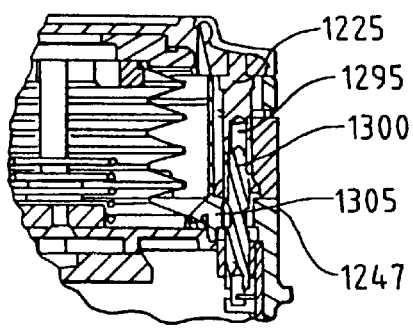

FIGS. 31A–31C are cross-sectional views illustrating operation of the latching mechanisms 1215. As illustrated, latch arm channels 1240 are dimensioned to engage the shaft portions 1245 of the conductive shafts 1225. As the latch arm 1230 is rotated to engage the shaft portions 1245, a nose portion 1280 of the latch arm 1230 cams against the surface 1285 of safety latch 1260 until it mates with channel 1290.

With the nose portion 1280 and corresponding channel 1290 in a mating relationship, latch arm 1230 is secured against inadvertent pivotal movement that would otherwise release removable contact assembly 1210 from secure engagement with the rotor base member 1205.

FIGS. 32A–32D are cross-sectional views of the rotor base member 1205 and removable contact assembly 1210 in an engaged state. As can be seen in these cross-sectional views, the electrically conductive shafts 1225 include a centrally disposed bore 1295 that receives a corresponding electrically conductive quick-connect pin 1300. It is through this engagement that an electrically conductive path is established between the rotor base member 1205 and the removable contact assembly 1210.

As also apparent from these cross-sectional views, the lower, interior portion of each latch arm 1230 includes a corresponding channel 305 that is shaped to engage the flange portions 1247 of the shafts 1225. Channel 1305 cams against corresponding surfaces of the flange portions 1247 to drive the shafts 1225 against surface 1310 which, in turn, effects a seal with O-ring 1275.

Rotor Contact Drive

Figure 34:
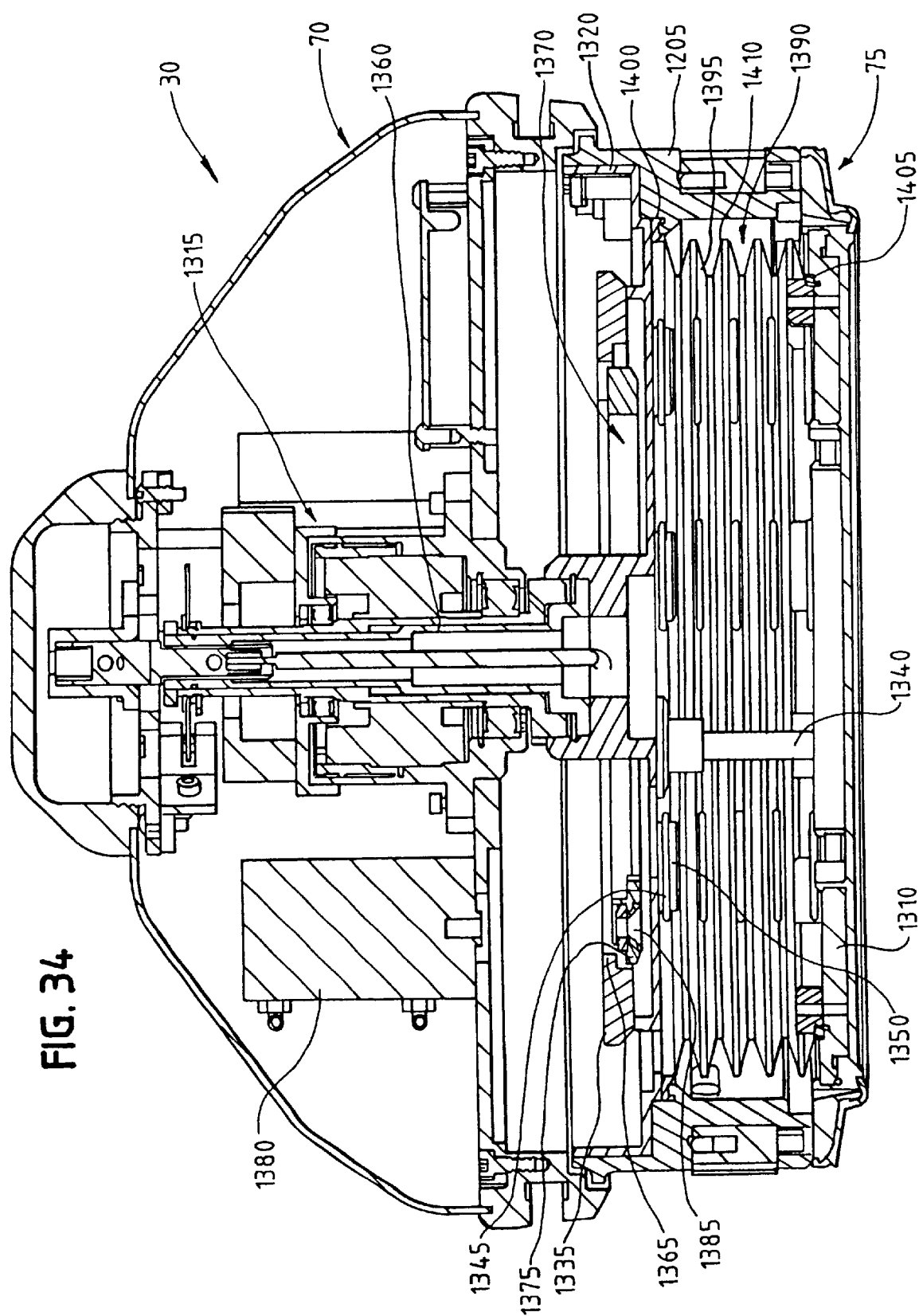
FIG. 34 is a cross-sectional view of the reactor head illustrating the disposition of the reactor head in a condition in which it is ready to present the workpiece to the reactor bowl.
Figure 35:
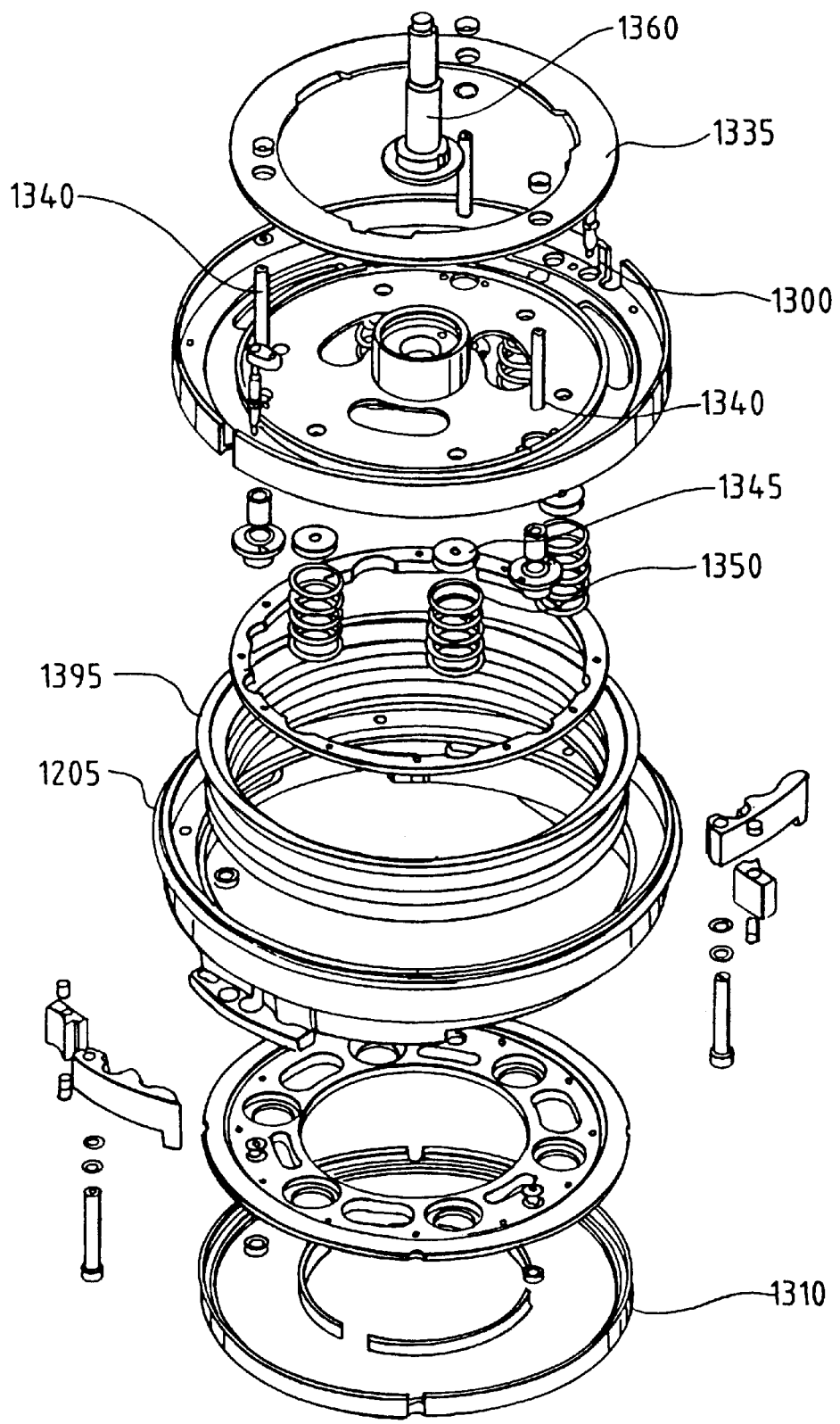
FIG. 35 illustrates an exploded view one embodiment of the rotor assembly.

As illustrated in FIGS. 33 and 34, the rotor assembly 75 includes an actuation arrangement whereby the wafer or other workpiece 25 is received in the rotor assembly by movement in a first direction, and is thereafter urged into-electrical contact with the contact assembly contact by movement of a backing member 1310 toward the contact assembly, in a direction perpendicular to the first direction. FIG. 35 is an exploded view of various components of the rotor assembly 75 and stationary assembly 70 of the reactor head 30.

As illustrated, the stationary assembly 70 of the reactor head 30 includes a motor assembly 1315 that cooperates with shaft 1360 of rotor assembly 75. Rotor assembly 75 includes a generally annular housing assembly, including rotor base member 1205 and an inner housing 1320. As described above, the contact assembly is secured to rotor base member 1205. By this arrangement, the housing assembly and the contact assembly 1210 together define an opening 1325 through which the workpiece 125 is transversely movable, in a first direction, for positioning the workpiece in the rotor assembly 175. The rotor base member 1205 preferably defines a clearance opening for the robotic arm as well as a plurality of workpiece supports 1330 upon which the workpiece is positioned by the robotic arm after the workpiece is moved transversely into the rotor assembly by movement through opening 1325. The supports 1330 thus support the workpiece 25 between the contact assembly 1210 and the backing member 1310 before the backing member engages the workpiece and urges it against the contact ring.

Reciprocal movement of the backing member 1310 relative to the contact assembly 1210 is effected by at least one spring which biases the backing member toward the contact assembly, and at least one actuator for moving the backing member in opposition to the spring. In the illustrated embodiment, the actuation arrangement includes an actuation ring 1335 which is operatively connected with the backing member 1310, and which is biased by a plurality of springs, and moved in opposition to the springs by a plurality of actuators.

With particular reference to FIG. 33, actuation ring 1335 is operatively connected to the backing member 1310 by a plurality (three) of shafts 1340. The actuation ring, in turn, is biased toward the housing assembly by three compression coil springs 1345 which are each held captive between the actuation ring and a respective retainer cap 1350. Each retainer cap 1350 is held in fixed relationship with respect to the housing assembly by a respective retainer shaft 1355. By this arrangement, the action of the biasing springs 1345 urges the actuation ring 1335 in a direction toward the housing, with the action of the biasing springs thus acting through shafts 1340 to urge the backing member 1335 in a direction toward the contact assembly 1210.

Actuation ring 1335 includes an inner, interrupted coupling flange 1365. Actuation of the actuation ring 1335 is effected by an actuation coupling 3170 (FIG. 34) of the stationary assembly 70, which can be selectively coupled and uncoupled from the actuation ring 1335. The actuation coupling 1370 includes a pair of flange portions 1375 that can be interengaged with coupling flange 1365 of the actuation ring 1335 by limited relative rotation therebetween. By this arrangement, the actuation ring 1335 of the rotor assembly 75 can be coupled to, and uncoupled from, the actuation coupling 1370 of the stationary assembly 70 of the reactor head 30.

With reference again to FIGS. 33 and 34, actuation coupling 1370 is movable in a direction in opposition to the biasing springs 1345 by a plurality of pneumatic actuators 1380 (shown schematically) mounted on a stationary, upper plate 1381 (see FIG. 1) of the stationary assembly 70. Each actuator 1380 is operatively connected with the actuation coupling 1370 by a respective linear drive member 1385, each of which extends generally through the upper plate 381 of the stationary assembly 70. There is a need to isolate the foregoing mechanical components from other portions of the reactor assembly 20. A failure to do so will result in contamination of the processing environment (here, a wet chemical electroplating environment). Additionally, depending on the particular process implemented in the reactor 20, the foregoing components can be adversely affected by the processing environment.

To effect such isolation, a bellows assembly 1390 is disposed to surround the foregoing components. The bellows assembly 1390 comprises a bellows member 395, preferably made from Teflon, having a first end thereof secured at 1400 and a second end thereof secured at 1405. Such securement is preferably implemented using the illustrated liquid-tight, tongue-and-groove sealing arrangement. The convolutes 1410 of the bellows member 1395 flex during actuation of the backing plate 1310.

FIG. 34 illustrates the disposition of the reactor head 30 in a condition in which it may accept a workpiece, while FIGS. 33 illustrates the disposition of the reactor head in a condition in which it is ready to process the workpiece in the reactor bowl 35.

Operation of the reactor head 30 will be appreciated from the above description. Loading of workpiece 25 into the rotor assembly 75 is effected with the rotor assembly in a generally upwardly facing orientation, such as illustrated in FIG. 2 with the processing head in a condition shown in FIG. 34. Workpiece 25 is moved transversely through the opening 325 defined by the rotor assembly 75 to a position wherein the workpiece is positioned in spaced relationship generally above supports 330. A robotic arm 415 is then lowered (with clearance opening 325 accommodating such movement), whereby the workpiece is positioned upon the supports 330. The robotic arm 415 can then be withdrawn from within the rotor assembly 75.

The workpiece 25 is now moved perpendicularly to the first direction in which it was moved into the rotor assembly. Such movement is effected by movement of backing member 1310 generally toward contact assembly 1210. It is presently preferred that pneumatic actuators 1380 act in opposition to biasing springs 1345 which are interposed between the inner housing 1320 and the spring plate 1311 of the backing member 1310. Thus, actuators 1380 are operated to allow conjoint movement of the actuator coupling 1370 and the actuator ring 1335 to permit springs 1345 to bias and urge the backing member 310 toward contact 1210.

In the preferred form, the connection between actuation ring 1335 and backing member 1310 by shafts 1340 permits some "float". That is, the actuation ring and backing member are not rigidly joined to each other. This preferred arrangement accommodates the common tendency of the pneumatic actuators 1380 to move at slightly different speeds, thus assuring that the workpiece is urged into substantial uniform contact with the electroplating contacts of the contact assembly 210 while avoiding excessive stressing of the workpiece, or binding of the actuation mechanism.

With the workpiece 25 firmly held between the backing member 310 and the contact assembly 210, lift and rotate apparatus 80 of FIG. 2 rotates the reactor head 30 and lowers the reactor head into a cooperative relationship with reactor bowl 35 so that the surface of the workpiece is placed in contact with the surface of the plating solution (i.e., the meniscus of the plating solution) within the reactor vessel.

Depending on the particular electroplating process implemented, it may be useful to insure that any gas which accumulates on the surface of the workpiece is permitted to vent and escape. Accordingly, the surface of the workpiece may be disposed at an acute angle, such as on the order of two degrees from horizontal, with respect to the surface of the solution in the reactor vessel. This facilitates venting of gas from the surface of the workpiece during the plating process as the workpiece, and associated backing and contact members, are rotated during processing. Circulation of plating solution within the reactor bowl 35, as electrical current is passed through the workpiece and the plating solution, effects the desired electroplating of a metal layer on the surface of the workpiece.

The actuation of the backing member 1310 is desirably effected by a simple linear motion, thus facilitating precise positioning of the workpiece, and uniformity of contact with the contacts of the contact assembly 1210. The isolation of the moving components using a bellows seal arrangement further increases the integrity of the electroless plating process.

A number of features of the present reactor facilitate efficient and cost-effective electroplating of workpieces such as semiconductor wafers. By use of a contact assembly having substantially continuous contact in the form of a large number of sealed, compliant discrete contact regions, a high number of plating contacts are provided while minimizing the required number of components. The actuation of the backing member 310 is desirably effected by a simple linear motion, thus facilitating precise positioning of the workpiece, and uniformity of contact with the contact ring. The isolation of the moving components using a bellows seal arrangement further increases the integrity of the electroplating process.

Maintenance and configuration changes are easily facilitated through the use of a detachable contact assembly 1210. Further, maintenance is also facilitated by the detachable configuration of the rotor assembly 75 from the stationary assembly 70 of the reactor head. The contact assembly provides excellent distribution of electroplating power to the surface of the workpiece, while the preferred provision of the peripheral seal protects the contacts from the plating environment (e.g., contact with the plating solution), thereby desirably preventing buildup of plated material onto the electrical contacts. The perimeter seal also desirably prevents plating onto the peripheral portion of the workpiece.

Electroless Plating Reactor

Figure 36:
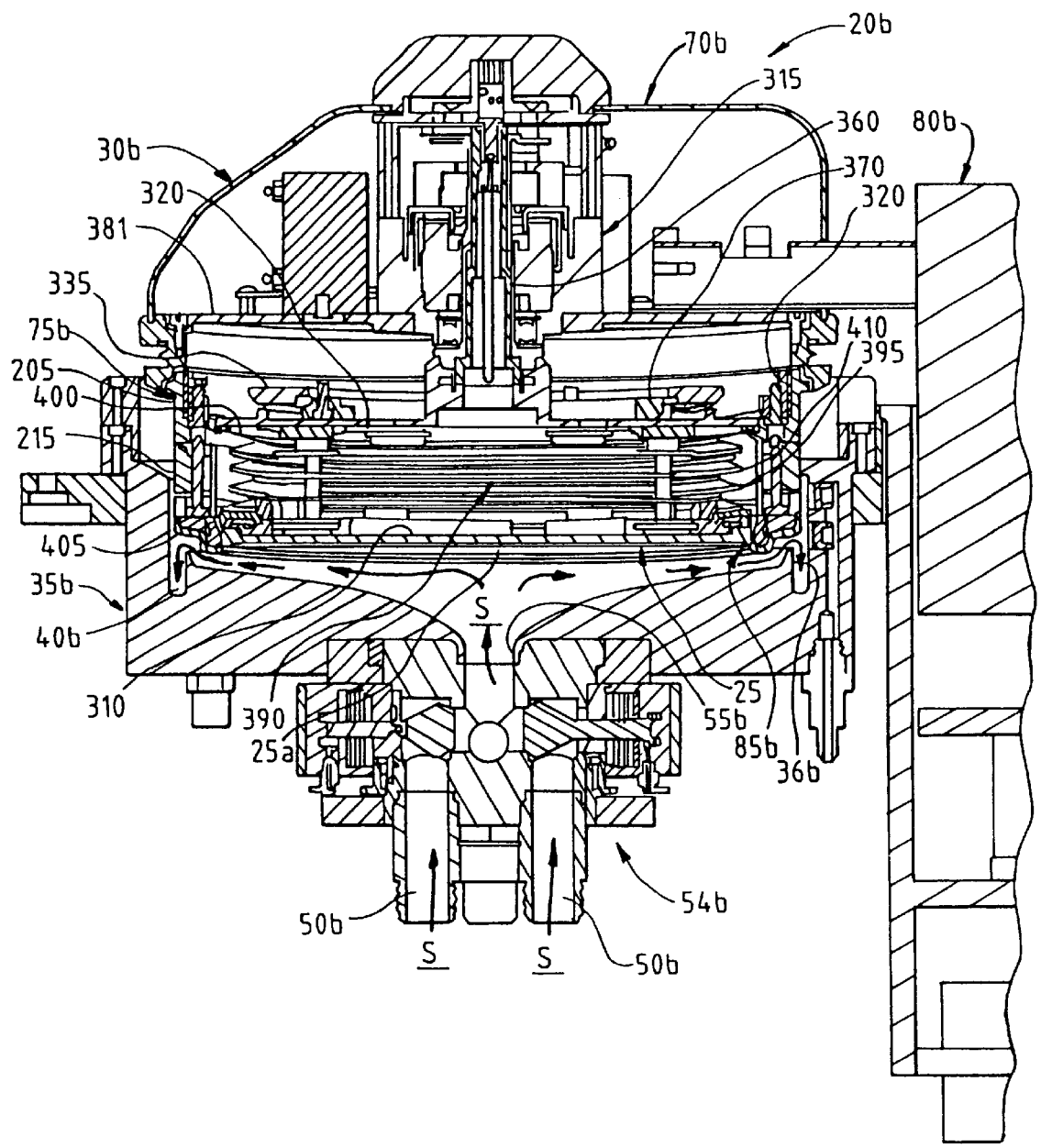
FIG. 36 is a cross-sectional view of one embodiment of an electroless plating reactor suitable for use in connection with the present inventions.

With reference to FIG. 36, there is shown a reactor assembly 20*b* for electroless plating on a microelectronic workpiece or workpiece, such as a semiconductor wafer 25. Generally stated, the reactor assembly 20*b* is comprised of a reactor head or processing head 30*b* and a corresponding reactor bowl 35*b*. This type of reactor assembly is particularly suited for effecting electroless plating of semiconductor wafers or like workpieces, in which a pre-applied thin-film seed layer of the wafer is plated with a blanket metallic layer.

The electroless plating reactor bowl 35*b* is that portion of the reactor assembly 20*b* that contains electroless plating solution, and that directs the solution against a generally downwardly facing surface of the workpiece 25*b* to be plated. To this end, electroless plating solution S is introduced into the reactor bowl 35*b*. The solution S flows from the reactor bowl 35*b*, over a weir-like inside wall 36*b* of the bowl, into a lower overflow channel 40*b* of the reactor assembly 20. The solution S exits the channel 40*b* through an outlet nozzle 41. The outlet nozzle 41*b* is connected by a conduit 42*b* to an outlet valve block 43*b* which can direct the solution S through one or two outlet passages 44*b*. An exhaust passage 45*b* directs gases to an exhaust nozzle 46*b* for collection, treatment and/or recycling. Solution can be drawn from the overflow chamber and collected, typically for recirculation back through the reactor.

Electroless plating solution flows from one or more inlet conduits 50*b* through a valve block 54*b* and then through a bottom opening 55*b* of the reactor bowl 35*b*. The solutionS contacts the downwardly facing, process side of the wafer 25.

The reactor head 30*b* of the reactor 20*b* is preferably constructed in the same manner as the electroplating reactor 20 of FIG. 1 and is comprised of a stationary assembly 70*b* and a rotor assembly 75*b*. Rotor assembly 75*b* is configured to receive and carry the wafer 25 or like workpiece, position the wafer in a process-side down orientation within the reactor bowl 35*b*, and to rotate or spin the workpiece during processing. The reactor head 30*b* is typically mounted on a lift/rotate apparatus 80*b*, which is configured to rotate the reactor head 30 from an upwardly-facing disposition (see FIG. 2), in which it receives the wafer to be plated, to a downwardly facing disposition, as shown in FIG. 35, in which the surface of the wafer to be plated is positioned downwardly in reactor bowl 35*b*. A robotic arm 415, including an end effector, is typically employed for placing the wafer 25 in position on the rotor assembly 75*b*, and for removing the plated wafer from the rotor assembly.

Unlike electroplating reactor 20, electroless plating reactor 20*b* does not conduct electrical power to the surface of wafer 25. As such, a workpiece support is used in lieu of an electrical contact assembly 85. To this end, the workpiece support may be constructed in the same fashion as any of the contact assemblies described above, except that the conductive structures (i.e., those constructed of platinized titanium or and other conductive metal) are constructed from a dielectric material that is compatible with the electroplating environment. As above, such workpiece holders preferably include provisions for providing a flow of an inert fluid, such as nitrogen, to the peripheral regions and backside of the wafer.

As particularly illustrated in FIGS. 37 through 41, the workpiece holder assembly 2085 may be generally comprised of several discrete components. An outer ring 2095 is formed from a plastic material or the like that is electrically non-conductive and is formed from a material that is chemically compatible with the electroless plating environment. The outer ring 2095 may, for example, be composed of PVDF. When the workpiece that is to be plated is a circular semiconductor wafer, the outer ring 2095, as well as the other portions of the workpiece holder assembly 2085, are formed as annular components that, when joined together, form a bounded central open region 2093 that exposes the surface of the semiconductor wafer that is to be plated.

The outer ring 2095 is provided with a radially extending end wall 95a having an oblique end region 2095b which forms an annular inside surface 2096 onto which is provided an annular seal element 2098. The seal element is adhesively adhered or molded or otherwise attached to the inside surface. As will be explained in further detail below, the seal element 2098 seals against the face 2025a of the semiconductor wafer 25 to assist in preventing the plating environment within the reactor bowl 35 from penetrating behind the wafer surface 25a which is to be plated. The annular seal element is preferably composed of AFLAS elastomer.

The outer ring 2095 surrounds a base ring 2100 which has a large body portion 2100a providing an inside groove 2100b and an outside groove 2100c. The base ring is preferably composed of stainless steel. The large body portion is connected to a collar portion 2100d which extends toward the inside surface 2096. The collar portion 2100d is turned inwardly at a lip 100e. A retainer ring 2102, preferably composed of polypropylene, is located within the base ring 2100. The retainer ring 2102 includes a centering flange 2102a, a conically extending wall 2102b, and an outside rib 2102c which interfits into the inside groove 2100b of the base ring 2100.

Located above the centering flange 2102a, and below the seal element 2098 is a "Belleville" spring 2104. The Belleville spring is annular in overall shape and generally rectangular in cross-section, and formed having a shallow frustoconical shape. The spring 2104 is held in place by the retainer ring 2102 and can be slightly pre-loaded (slightly flattened) by the retainer ring 2102 against the seal element 2098. The spring 2104 includes an outside annular notch 2104a, and an inside annular notch 2104b. The spring 2104 is preferably composed of plastic.

Two connector shafts 2225 are threaded into threaded holes 2226 diametrically oriented across the workpiece holding assembly 2085, and formed into the base ring 2100. The shafts 2225 include tool engagement shoulders 2227 for tightening the shafts 2225 into the base ring 100.

Preferably, workpiece support 2085 includes a plurality of passages for providing a purging gas to the peripheral regions of the wafer radially exterior of the seal element 2098 as well as to the back side of the wafer 25. To this end, as illustrated in FIGS. 40 and 41, the workpiece support 2085 includes an annular channel 2137 that is in fluid communication with a purge port (not illustrated) and effectively functions as a manifold. A plurality of slots 2139 are formed in the interstitial region between the outer ring 2095 and the base ring 2100 to provide fluid communication between the annular channel 2137 and region 2141 proximate the peripheral edge regions of the wafer 25. Together, seal member 2098 and the flow of purging gas assist in forming a barrier between the electroplating environment and the peripheral regions and backside of wafer 25. Further distribution of the purging gas is affected through an annular channel 2143 formed between the exterior of retainer ring 2102 and base ring 2100.

During loading of the wafer 25 into the workpiece holding assembly 2085, the wafer 25 progresses upwardly in the direction Y1 to the position shown in FIG. 40. The wafer is radially guided or centered by the conically shaped wall 2102b to its position shown in FIG. 40. In the position shown in FIG. 40, the wafer 25 engages the inside annular notch 2104b of the spring 2104. By action of a backing member 310, described above, the wafer 25 is pressed upwardly, acting to flex the spring 2104 into the position shown in FIG. 41.

The flexing or flattening of the spring 2104, as shown in FIG. 41, causes the wafer 25 to be partially received within the notch 2104b, and the lip 2100e to be received in the outside notch 2104a. The wafer face 25a is pressed against the seal element 2098 which is in turn held in place by the annular inside surface 2096 of the outer ring 2095. When the backing member 310 is released, the spring 2104, under influence of its own resilient spring energy, will return to its configuration shown in FIG. 40 and partially push the wafer 25 in the direction Y2. From the position shown in FIG. 40 absent the force exerted by the backing member 310, the wafer 25 will proceed by gravity supported on the retracting backing member 310 along the direction Y2.

Figure 42:
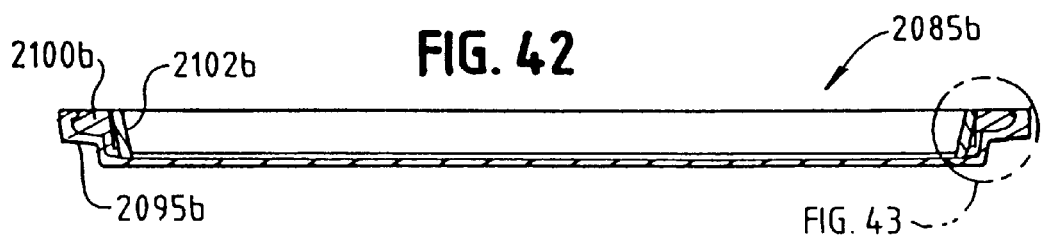
Figure 43:
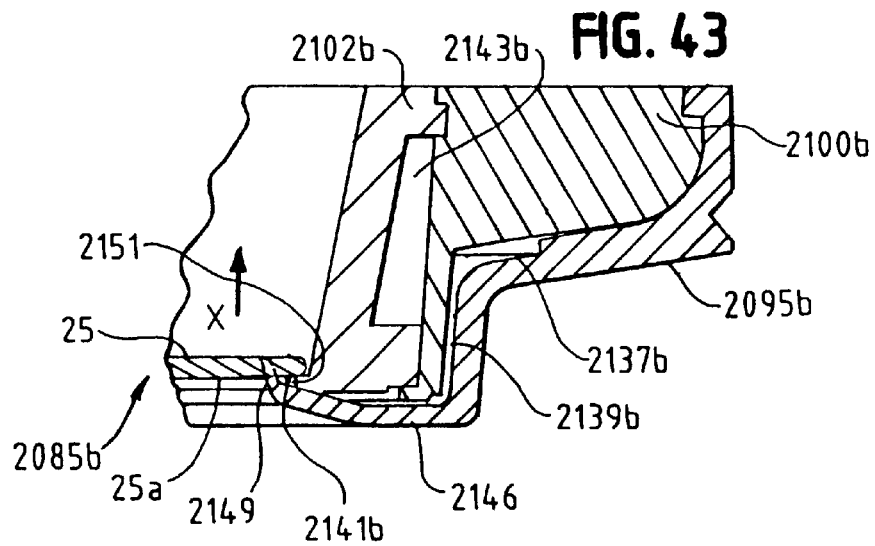

A further embodiment of a workpiece holder is illustrated at 2085b of FIGS. 42 and 43. As illustrated, workpiece support 2085b is substantially similar to workpiece support 2085 of FIGS. 37–41. There are, however, three notable differences. First, a separate seal element 2098 is not employed in this embodiment. Rather, outer ring 2095b includes an annular extension 2146 that terminates in an upturned lip 2149 that engages surface 25a of wafer 25. Second, upturned lip 2149 assists in removing wafer 25 from the wafer holder 2085b by providing a biasing force in the direction of the arrow X when backing member 310 is disengaged from the wafer 25. As a result, Belleville ring member 2104 is not employed in this embodiment. Finally, an annular lip 2151 is provided on retainer ring 2102b to as a limit member that sets the limits to which wafer 25 may be moved into engagement with wafer holder 2085b.

The embodiment illustrated in FIGS. 42 and 43, like wafer holder 2085, also includes a plurality of flow channels for the provision of a purging gas. Given the substantial similarities between wafer holder 2085 and wafer holder 2085b, similar structures are labeled with similar reference news in the embodiment of wafer holder 2085b.

Purge Gas Supply to Contact and Holder Assemblies

Figure 44:
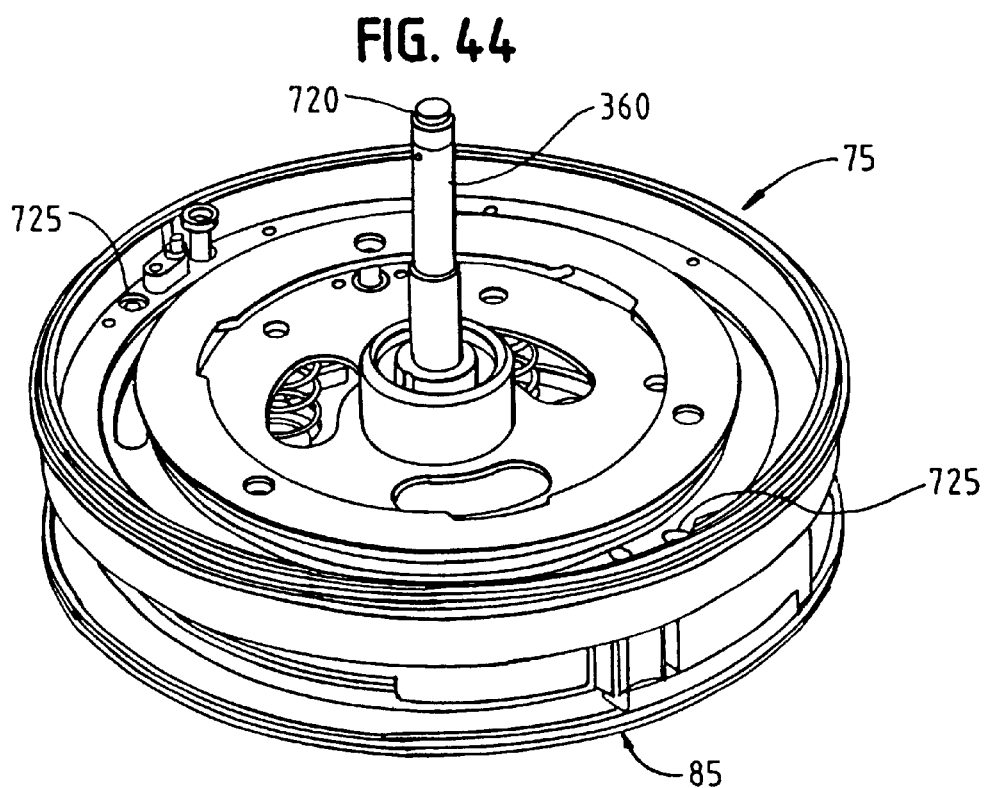
FIGS. 44–46 illustrate one manner in which a purging gas, such as nitrogen, can be supplied to either a workpiece holder or contact assembly that is constructed in accordance with the disclosed embodiments.
Figure 45:
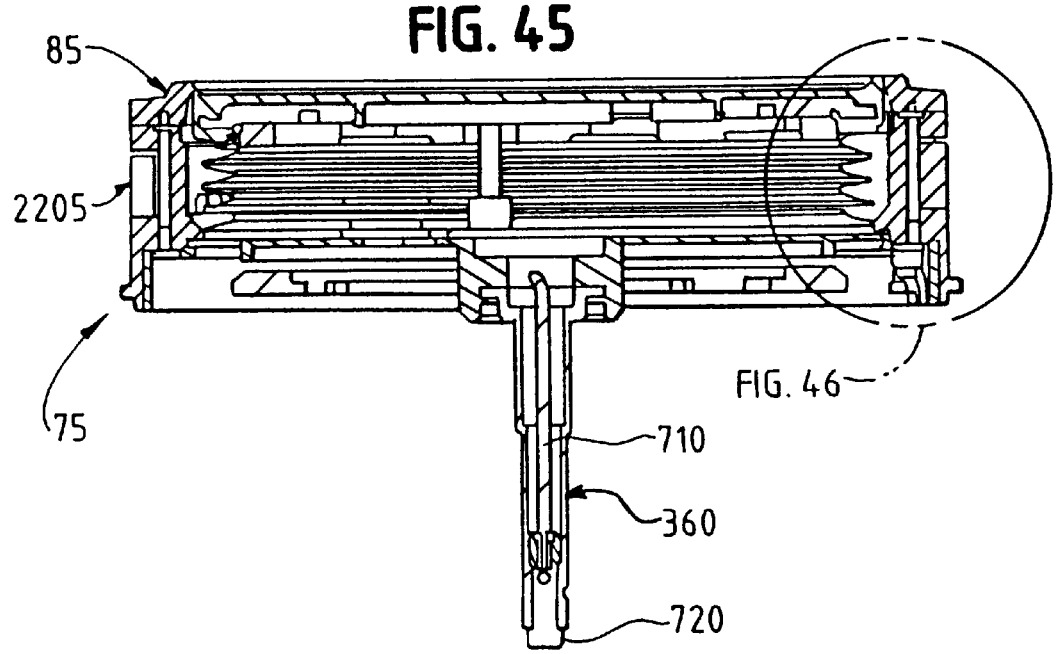
Figure 46:
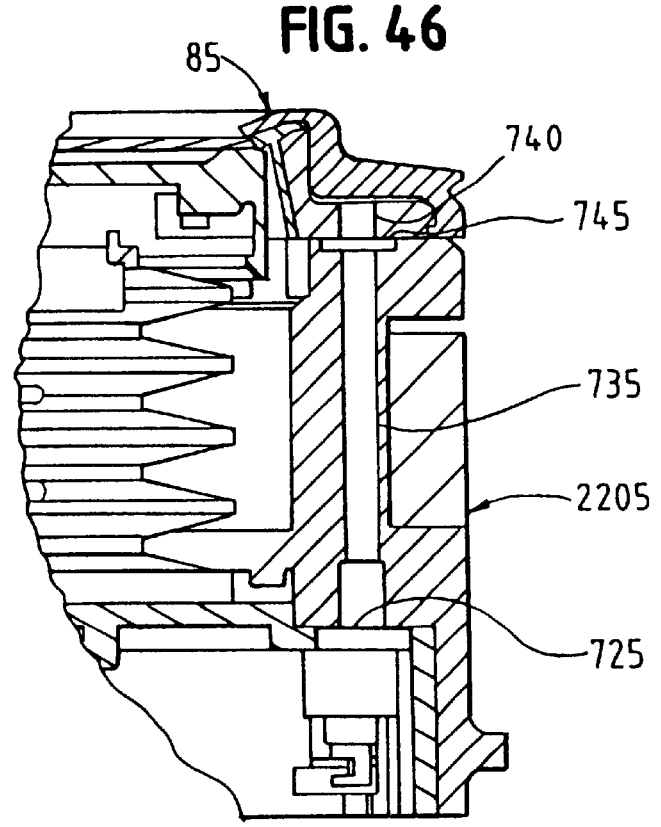

When any of the contact assemblies or workpiece holders described above include a fluid communication network that provides a purging gas, such as nitrogen, it must be supplied from a source exterior to the contact assembly or workpiece holder. FIGS. 44–46 illustrate one manner in which such a fluid communication network may be supplied with a purging gas.

With reference to FIGS. 44 and 45, the rotor assembly 75 may be provided with a fluid communication channel or tube 710 having an inlet at 720 that receives the purging gas and communicates it to one or more purge ports 725 that are disposed proximate the peripheral regions of the workpiece holder or contact assembly, shown here as assembly 85a. In the illustrated embodiment, a tube 710 is used for such fluid communication. The tube 710 extends through the hollowed center of drive shaft 360 and then proceeds from the region of drive shaft 360 that is proximate the workpiece holder or contact assembly to at least one purge port 725 (two purge ports being used in the illustrated embodiment). In the alternative, the fluid communication path represented here by tube 710 may comprise one or more channels that are formed as hollow regions in solid body portions of the rotor assembly 75. For example, as noted above, the purge gas may be supplied directly through a hollowed region of drive shaft 360 as opposed to an intermediate tube. Depending on the particular implementation of the rotor assembly 75, communication of the purging gas may then proceed to the purge port through a corresponding tube or through a hollow channel formed in a substantially solid body member that spans therebetween.

Communication of the purging gas from purge port 725 to the isolated regions of the corresponding workpiece holder or contact assembly is illustrated in FIG. 46. As shown, purge port 725 opens to a purge passageway 735 that is disposed through an outer housing of the rotor assembly 75. The purge passageway 735 opens to an inlet port 740 of the workpiece holder or contact assembly (such inlet ports are also illustrated in the embodiments of the workpiece holders and contact assemblies described above). From such inlet ports, the purge gas flows through the particular holder or contact assembly in the manner described above.

Integrated Plating Tool

Figure 47:
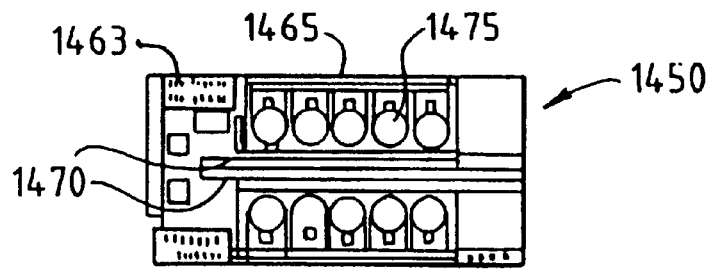
FIGS. 47–49 are top plan views of integrated processing tools that may incorporate electroless plating reactors and electroplating reactors in combination.
Figure 48:
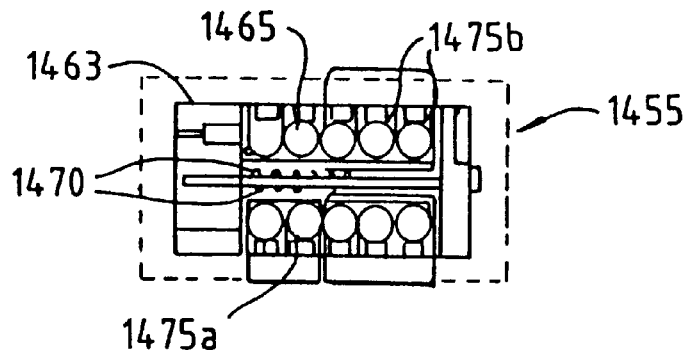
Figure 49:
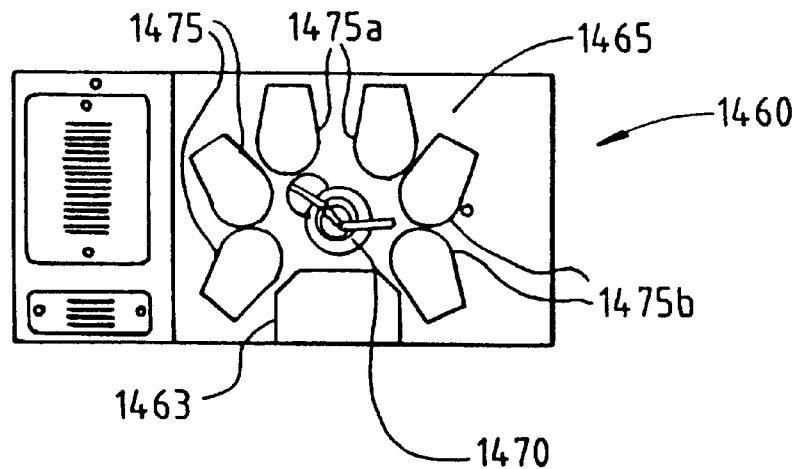

FIGS. 47 through 49 are top plan views of integrated processing tools, shown generally at 1450, 1455, and 1500 that may incorporate electroless plating reactors and electroplating reactors as a combination for plating on a microelectronic workpiece, such as a semiconductor wafer. Processing tools 1450 and 1455 are each based on tool platforms developed by Semitool, Inc., of Kalispell, Mont. The processing tool platform of the tool 450 is sold under the trademark LT-210™, the processing tool platform of the tool 1455 is sold under the trademark LT-210C™, and the processing tool 1500 is sold under the trademark EQUINOX™. The principal difference between the tools 1450, 1455 is in the footprints required for each. The platform on which tool 1455 is based has a smaller footprint than the platform on which tool 1455 is based. Additionally, the platform on which tool 1450 is based is modularized and may be readily expanded. Each of the processing tools 1450, 4155, and 1500 are computer programmable to implement user entered processing recipes.

Each of the processing tools 1145, 1455, and 1500 include an input/output section 1460, a processing section 1465, and one or more robots 1470. The robots 1470 for the tools 1450, 1455 move along a linear track. The robot 1470 for the tool 1500 is centrally mounted and rotates to access the input/output section 1460 and the processing section 1465. Each input/output section 1460 is adapted to hold a plurality of workpieces, such as semiconductor wafers, in one or more workpiece cassettes. Processing section 1465 includes a plurality of processing stations 1475 that are used to perform one or more fabrication processes on the semiconductor wafers. The robots 1470 are used to transfer individual wafers from the workpiece cassettes at the input/output section 1460 to the processing stations 1475, as well as between the processing stations 1475.

One or more of the processing stations 1475 can be configured as electroless plating reactor 1475*a* such as heretofore described, and one or more of the processing stations can be configured as electroplating assemblies, 1475*b* such as the electroplating reactor described above. For example, each of the processing tools 1450 and 1455 may include three electroless plating reactors, three electroplating reactors and one or more pre-wet/rinse station or other processing vessel. The pre-wet/rinse station is preferably one of the type available from Semitool, Inc. It will now be recognized that a wide variation of processing station configurations may be used in each of the individual processing tools 450, 455, and 500 to execute electroless plating and electroplating processes. As such, the foregoing configurations are merely illustrative of the variations that may be used.

Plating Method Using Electroless Plating and Electroplating

Figure 50:
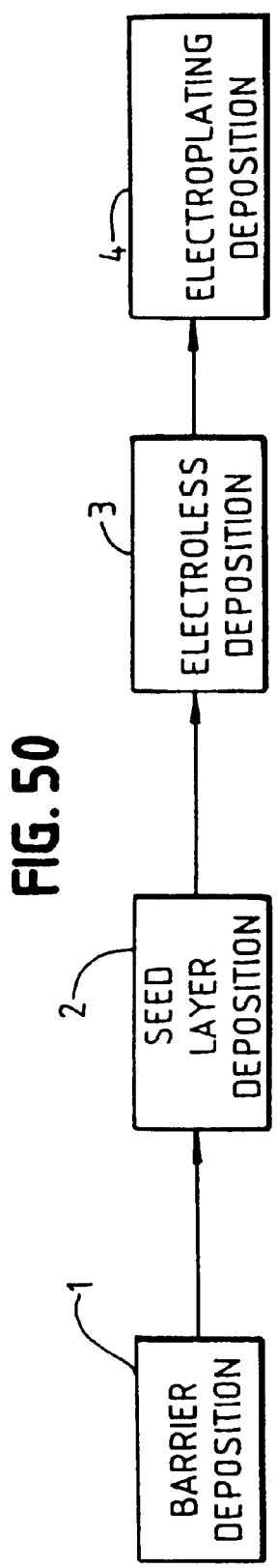
FIG. 50 is a flow diagram illustrating a process for plating a workpiece that incorporates both electroless and electroplating steps.

According to a method of the present invention, workpieces, such as semiconductors wafers, having first been processed to have a seed layer applied thereon, are electrolessly plated and then electroplated. The method is schematically described in FIG. 50.

A barrier layer is first applied (step 1) to features on a surface of a workpiece. The barrier layer can be applied by PVD or CVD processes. A seed layer is then applied (step 2) onto the barrier layer. The seed layer is preferably a Cu seed layer applied by a PVD or CVD processes. After the seed layer is applied, the workpiece can be placed in an electroless plating reactor as described below. An electroless plating bath is provided in the reactor and the workpiece is exposed to the plating bath to plate a conductive layer, preferably copper, thereon (step 3). The conductive layer is applied as a blanket to the extent that small and high aspect ratio vias and trenches are filled, but not to the extent that large vias and trenches are completely filled. By terminating the electroless plating at this point, a shorter time period in the overall process can be achieved. The workpiece having the electrolessly plated conductive layer thereon is then removed from the electroless plating reactor and transferred to an electroplating reactor wherein a further conductive layer, preferably copper is applied over the electrolessly plated conductive layer (step 4). The electroplating process has a higher deposition rate and has adequate filling conformality to fill the larger trenches and vias.

The electroless plating recipe can be a known recipe such as disclosed in the background section of this application in the article by V. M. Dubin, et al., or as describe in U.S. Pat. Nos. 5,500,315; 5,310,580; 5,389,496; or 5,139,818, all incorporated herein by reference. Further, the foregoing processing sequence can be carried out in any of the tools illustrated in FIGS. 47–49.

Numerous modifications may be made to the foregoing system without departing from the basic teachings thereof. Although the present invention has been described in substantial detail with reference to one or more specific embodiments, those of skill in the art will recognize that changes may be made thereto without departing from the scope and spirit of the invention as set forth in the appended claims.

What is claimed is:

1. A contact assembly for providing electrical contact between a workpiece and a source of electrical power, the contact assembly comprising:

a body member having an inner wall defining an open region sized larger than the workpiece;

a contact system having a plurality of cantilevered spring contacts extending at least generally radially inwardly with respect to the inner wall to a location in the open region; and a barrier member having a radially transverse portion projecting inwardly from the body and into the open region, the barrier having a lip radially inwardly from the spring contacts defining a processing aperture sized smaller than the workpiece, wherein the lip is configured to contact the workpiece.

2. A contact assembly as claimed in claim 1 wherein the plurality of contact are in the form of discrete flexure contacts.

3. A contact assembly as claimed in claim 2 wherein the flexure contacts extend radially inward toward the center.

4. A contact assembly as claimed in claim 1 wherein the spring contacts extend inward at an angle with respect to a radius of the processing aperture.

5. A contact assembly as claimed in claim 2 wherein some of the flexure contacts have a greater length than the remaining flexure contacts.

6. A contact assembly as claimed in claim 2 wherein at least some of the plurality of flexure contacts each include an upstanding portion, a transverse portion, a vertical portion, and a wafer contact portion.

7. A contact assembly as claimed in claim 1 wherein the plurality of contacts are adapted for executing a wiping action against the surface of the workpiece as the workpiece is brought into engagement with the contacts.

8. A contact assembly as claimed in claim 1 further comprising a contact support member for captivating at least a portion of the plurality of contacts within a channel defined between the contact support member and the outer body member, the contact support member being disposed radially interior of the outer body member.

9. A contact assembly as claimed in claim 8 wherein the contact support member includes a groove, and the contact assembly further comprises a wedge member disposed to engage said groove along with the discrete flexures to thereby secure the contacts with the contact support member.

10. A contact assembly as claimed in claim 9 wherein at least a portion of the wedge member assists in stiffening the flexing of the contacts as a workpiece is brought into engagement with the contact assembly.

11. A contact assembly as claimed in claim 1 wherein the plurality of contacts are comprised of platinized titanium.

12. A contact assembly as claimed in claim 1 wherein the outer body is comprised of a dielectric material.

13. A contact assembly as claimed in claim 1 wherein the plurality of flexure contacts are integrated with a corresponding common ring.

14. A contact assembly as claimed in claim 1, wherein the contacts are in the form of a Belleville ring contact.

15. A contact assembly as claimed in claim 1 wherein the barrier member comprises a lip formed integrally with the outer body member adapted for engaging the surface of the workpiece.

16. A contact assembly as claimed in claim 1 wherein the barrier member comprises an elastomeric seal member supported by the outer body member, the elastomeric seal member adapted for engaging the surface of the workpiece.

17. The contact assembly of claim 1 wherein the contact system further comprises a conductive ring and the cantilevered spring contacts of the contact system comprise fingers integral with the conductive ring that project radially inwardly along a radius of the open region and upwardly at an acute angle with respect to a plane defined by the open region of the body.

18. The contact assembly of claim 1 wherein the contact system further comprises a conductive ring and the cantilevered spring contacts of the contact system comprise fingers integral with the conductive ring that project generally radially inwardly from the conductive ring at an angle with respect to a radius of the open region and upwardly at an acute angle with respect to a plane defined by the open region of the body.

19. The contact assembly of claim 1 wherein the contact system further comprises a conductive ring and the cantilevered spring contacts of the contact system comprise fingers integral with the conductive ring that project radially inwardly from the conductive ring along a radius of the open region.

20. The contact assembly of claim 1 wherein the cantilevered spring contacts of the contact system comprise individual flexure members attached to the body by a wedge, the flexure members having a cantilevered finger projecting radially inwardly from the body to an interior portion of the open region.

21. A contact assembly for providing electrical contact between a workpiece and a source of electrical power in electroplating applications, the contact assembly comprising:
  a conductive mount member having a generally annular shape with an opening sized to receive the workpiece, the mount member being the primary support structure of the contact assembly;
  a dielectric outerbody attached to the mount member, the outerbody having a barrier section projecting inwardly with respect to the mount member to an interior lip sized to engage a perimeter portion of the workpiece; and
  a plurality of flexing contact members electrically coupled to the mount member, the flexing contact members having a first end at least proximate to the mount member and a second end projecting inwardly from the first end to a location between the interior lip of the outerbody and the mount member, the first end of the contact members defining contact points that engage the workpiece and elastically couple the workpiece to the mount member.

22. A contact assembly for providing electrical contact between a workpiece and a source of electrical power in electroplating applications, the contact assembly comprising:
  a primary support structure, the primary support structure being a conductive ring having an outer annular surface, an inner annular surface, a top surface and a bottom surface, the inner annular surface being sized to allow the workpiece to pass through the primary support structure;
  an outerbody attached to the primary support structure, the outerbody having an annular barrier section projecting radially inwardly with respect to the inner annular surface of the primary support structure to an interior lip sized to engage a perimeter portion of the workpiece; and
  a contact system having a plurality of contact members electrically coupled to the primary support structure, the contact members having a first end at least proximate to the inner annular surface of the primary support structure and a second end defining a contact point to electrically engage the workpiece, the first ends of the contact members being generally stationary relative to the primary support structure and the second ends of the contact members projecting inwardly from the first ends to locations between the interior lip of the outerbody and the inner annular surface.

23. The contact assembly of claim 22 wherein the plurality of contact members comprises individual flexure members spaced apart from one another around the primary support structure, each flexure member having an upstanding portion contacting the support structure and a transverse portion projecting inwardly from the upstanding portion to extend inwardly with respect to the inner annular surface of the primary support member.

24. The contact assembly of claim 22 wherein the contact system further comprises a conductive arcuate member and the contact members comprise a plurality of generally flat fingers projecting inwardly from the conductive arcuate member, the conductive arcuate member being coupled to the primary support structure so that the fingers extend generally radially inwardly with respect to the inner annular surface of the primary support structure upwardly at an acute angle with respect to a plane defined by the bottom surface of the primary support structure.

25. A contact assembly for providing electrical contact between a workpiece and a source of electrical power, the contact assembly comprising:

a primary support structure having an outer wall, an inner wall, a first surface between the outer wall and the inner wall, and a second surface between the outer wall and the inner wall, wherein the inner wall defines a receiving opening larger than the microelectric workpiece;

a barrier projecting inwardly with respect to the inner wall of the primary support structure to an interior lip configured to engage a perimeter portion of the workpiece, the interior lip of the barrier section defining a processing opening smaller than the microelectronic workpiece; and a conductive contact system attached to the primary support structure, the contact system having plurality of contact members that have a base end at least proximate to the primary support structure and a contact end projecting inwardly with respect to the inner wall to a location between the interior lip of the outerbody and the inner wall, wherein the contact members flex about the base ends toward the barrier section when the workpiece engages the contact ends and moves through the receiving opening toward the second surface of the primary support member.

26. The contact assembly of claim 25 wherein:
the primary support structure comprises an electrically conductive ring; and
the barrier comprises a dielectric outer body attached to the electrically conductive ring.

27. The contact assembly of claim 25 wherein the contact system further comprises an annular conductive ring having an opening and the contact members comprise a plurality of cantilevered tabs projecting inwardly from the conductive ring toward the opening.

28. The contact assembly of claim 25 wherein the contact system comprises a plurality of individual flexure members such that each flexure member defines a contact member.

29. A contact assembly for providing electrical contact between a workpiece and a source of electrical power in electroplating applications, the contact assembly comprising:

a primary support structure having an inner wall defining an open region sized larger than the workpiece; and a contact system coupled to the primary support structure, the contact system having a plurality of cantilevered spring contacts extending at least generally radially inwardly with respect to the inner wall to a location in the open region, the cantilevered spring contacts having a pivoting end at least proximate to the primary support structure and a contact end in the open region, wherein the cantilevered spring contacts flex as a workpiece engages the contact ends and moves through the open region causing the contact ends to move laterally across a front surface of the workpiece.

30. The contact assembly of claim 29 wherein the contact system further comprises a conductive ring, and wherein the pivoting ends of the spring contacts are integral with the conductive ring and the contact ends of the spring contacts project radially inwardly from the conductive ring along a radius of the open region.

31. The contact assembly of claim 29 wherein the contact system further comprises a conductive ring, and wherein the pivoting ends of the spring contacts are integral with the conductive ring and the contact ends of the spring contacts project generally radially inwardly from the conductive ring at an angle with respect to a radius of the open region.

32. The contact assembly of claim 29 wherein the contact system further comprises a conductive ring, and wherein the pivoting ends of the spring contacts are integral with the conductive ring and the contact ends of the spring contacts project radially inwardly from the conductive ring along a radius of the open region and upwardly at an acute angle with respect to a plane defined by the open region.

33. The contact assembly of claim 29 wherein the contact system further comprises a conductive ring, and wherein the pivoting ends of the spring contacts are integral with the conductive ring and the contact ends of the spring contacts project generally radially inwardly from the conductive ring at an angle with respect to a radius of the open region and upwardly at an acute angle with respect to a plane defined by the open region.

34. The contact assembly of claim 29, further comprising a barrier having a transverse section projecting radially inwardly with respect to the inner wall of the primary support structure to an interior lip radially inward of the contact ends of the contact members, wherein the lip of the barrier is configured to engage a perimeter portion of the workpiece.

35. The contact assembly of claim 34 wherein:
the primary support structure comprises an electrically conductive ring; and
the barrier comprises a flexible dielectric outer-body having a first section attached to the primary support structure and a second section extending transverse to the first section, the second section of the dielectric outer-body defining the transverse section of the barrier.

36. The contact assembly of claim 35 wherein the contact system further comprises a conductive ring, and wherein the pivoting ends of the spring contacts are integral with the conductive ring and the contact ends of the spring contacts project radially inwardly from the conductive ring along a radius of the open region.

37. The contact assembly of claim 35 wherein the contact system further comprises a conductive ring, and wherein the pivoting ends of the spring contacts are integral with the conductive ring and the contact ends of the spring contacts project generally radially inwardly from the conductive ring at an angle with respect to a radius of the open region.

38. The contact assembly of claim 35 wherein the contact system further comprises a conductive ring, and wherein the pivoting ends of the spring contacts are integral with the conductive ring and the contact ends of the spring contacts project radially inwardly from the conductive ring along a radius of the open region and upwardly at an acute angle with respect to a plane defined by the open region.

39. The contact assembly of claim 35 wherein the contact system further comprises a conductive ring, and wherein the pivoting ends of the spring contacts are integral with the conductive ring and the contact ends of the spring contacts project generally radially inwardly from the conductive ring at an angle with respect to a radius of the open region and upwardly at an acute angle with respect to a plane defined by the open region.

* * * * *

UNITED STATES PATENT AND TRADEMARK OFFICE
CERTIFICATE OF CORRECTION

PATENT NO. : 6,309,524 B1
DATED : October 30, 2001
INVENTOR(S) : Woodruff et al.

It is certified that error appears in the above-identified patent and that said Letters Patent is hereby corrected as shown below:

Column 3,
Line 48, delete period between "uncollimated" and "Ta";
Line 62, "seedibarrier" should be -- seed/barrier --;

Column 4,
Line 11, insert comma between "advantages" and "such";
Line 58, insert -- a -- between "with" and "further";
Line 65, "reactor as may" should be -- reactor may --;

Column 6,
Line 1, insert -- of -- between "view" and "embodiment";

Column 11,
Line 15, insert comma between "illustrated" and "the";
Line 61, insert -- the -- between "to" and "backside";

Column 12,
Line 43, "preferably in formed" should be -- preferably formed --;

Column 14,
Line 4, insert -- to -- between "730" and "effect";

Column 18,
Line 1, "purge the asked" should be -- delivering purge gas --;

Column 19,
Line 25, "into-" should be -- into --;

Column 22,
Line 7, "workpiece" should be -- workpieces --;
Line 59, "or and other" should be -- another --;

Column 25,
Line 26, "450" should be -- 1450 --;
Line 30, "1450," should be -- 1450 and --;
Line 35, "4155" should be -- 1455 --;

UNITED STATES PATENT AND TRADEMARK OFFICE
CERTIFICATE OF CORRECTION

PATENT NO. : 6,309,524 B1
DATED : October 30, 2001
INVENTOR(S) : Woodruff et al.

It is certified that error appears in the above-identified patent and that said Letters Patent is hereby corrected as shown below:

<u>Column 26,</u>
Line 11, "by a PVD" should be -- by PVD --;
Line 31, "describe" should be -- described --;

<u>Column 28,</u>
Line 25, "elastically" should be -- electrically --;
Line 59, insert -- primary -- between "contacting" and "the";

Signed and Sealed this

Eleventh Day of February, 2003

JAMES E. ROGAN
*Director of the United States Patent and Trademark Office*